(12) United States Patent
Hefetz et al.

(10) Patent No.: US 10,054,698 B2
(45) Date of Patent: Aug. 21, 2018

(54) TEMPERATURE STABILIZATION FOR DETECTOR HEADS

(71) Applicant: General Electric Company, Schenectady, NY (US)

(72) Inventors: Yaron Hefetz, Tirat Carmel (IL); Raed Khamaisi, Tirat Carmel (IL)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/253,132

(22) Filed: Aug. 31, 2016

(65) Prior Publication Data

US 2018/0059270 A1    Mar. 1, 2018

(51) Int. Cl.
*G01T 7/00* (2006.01)
*G01T 1/161* (2006.01)
*H05K 7/20* (2006.01)

(52) U.S. Cl.
CPC ............... *G01T 7/00* (2013.01); *G01T 1/161* (2013.01); *H05K 7/2039* (2013.01); *H05K 7/20245* (2013.01)

(58) Field of Classification Search
CPC ..................................................... G01T 7/00
See application file for complete search history.

(56) References Cited

U.S. PATENT DOCUMENTS

| | | | |
|---|---|---|---|
| 7,511,277 B2 | 3/2009 | Ueno et al. | |
| 2004/0075059 A1* | 4/2004 | Serebryanov | G01T 1/1648 250/370.15 |
| 2011/0036988 A1* | 2/2011 | Campbell | G01T 1/026 250/370.07 |
| 2011/0248177 A1* | 10/2011 | Crocker | H01L 23/3677 250/370.15 |
| 2015/0094574 A1 | 4/2015 | Bouhnik et al. | |
| 2016/0022228 A1 | 1/2016 | Khen et al. | |
| 2016/0146949 A1* | 5/2016 | Frach | G01T 1/1642 250/362 |

OTHER PUBLICATIONS

Invitation to Pay Additional Fee for corresponding PCT application No. PCT/US2017/047325 dated Oct. 23, 2017; 11 pages.
International Search Report and Written Opinion for corresponding PCT application No. PCT/US2017/047325 dated Dec. 18, 2017; 15 pages.

* cited by examiner

*Primary Examiner* — Hugh H Maupin
(74) *Attorney, Agent, or Firm* — Dean D. Small; The Small Patent Law Group, LLC

(57) ABSTRACT

An imaging system is provided that includes a gantry, plural radiation detector head assemblies, a cooling unit, and a manifold. The radiation detector head assemblies are disposed about a bore of the gantry. Each radiation detector head assembly includes a detector housing and a rotor assembly. The rotor assembly is configured to be rotated about an axis. The rotor assembly includes a detector unit that in turn includes an absorption member and associated processing circuitry. The cooling unit is mounted to the gantry and is configured to provide an output flow of air at a controlled temperature. The manifold is coupled to the cooling unit and the plural radiation detector head assemblies, and places the cooling unit and radiation detector head assemblies in fluid communication with each other. The output flow of air from the cooling unit is delivered to the plural radiation detector head assemblies.

19 Claims, 18 Drawing Sheets

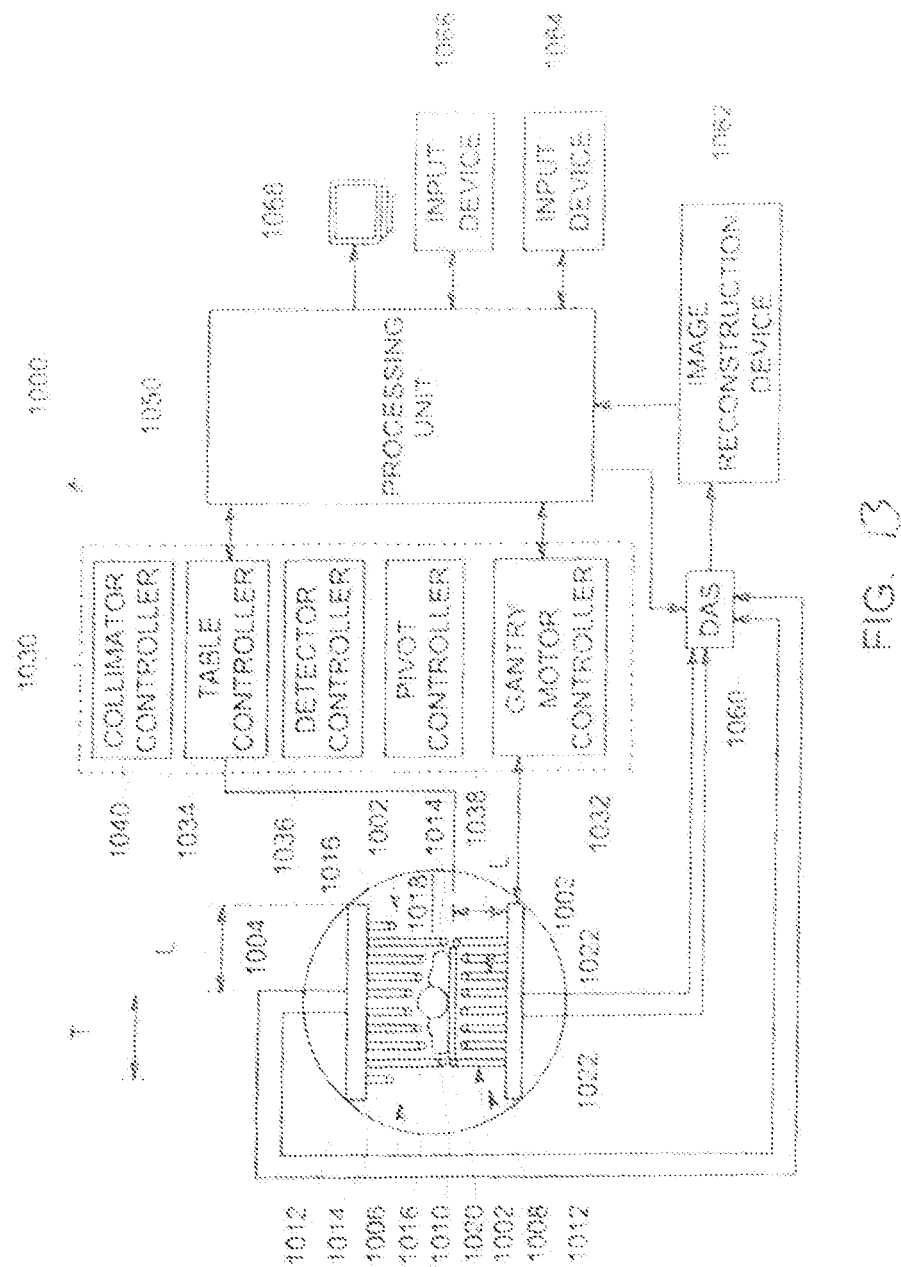

TEMPERATURE STABILIZATION FOR DETECTOR HEADS

BACKGROUND

The subject matter disclosed herein relates generally to medical imaging systems, and more particularly to reduction of airborne radiation contamination for detector heads.

In nuclear medicine (NM) imaging, such as single photon emission computed tomography (SPECT) or positron emission tomography (PET) imaging, radiopharmaceuticals may be administered internally to a patient. Detectors (e.g., gamma cameras), typically installed on a gantry, capture the radiation emitted by the radiopharmaceuticals and this information is used, by a computer, to form images. The NM images primarily show physiological function of for example, the patient or a portion of the patient being imaged. Detectors, however, may be subject to changes in performance, or in changes to the signals produced by detectors. For example, changes in temperature can affect the energy levels reported by a detector for radiation events impacting the detector.

BRIEF DESCRIPTION

In accordance with an embodiment, an imaging system is provided that includes a gantry, plural radiation detector head assemblies, a cooling unit, and a manifold. The gantry has a bore. The radiation detector head assemblies are disposed about the bore of the gantry. Each radiation detector head assembly includes a detector housing a rotor assembly. The rotor assembly is disposed within the detector housing and configured to be rotated about an axis. The rotor assembly includes a detector unit that in turn includes an absorption member and associated processing circuitry. The cooling unit is mounted to the gantry and is configured to provide an output flow of air at a controlled temperature. The manifold is coupled to the cooling unit and the plural radiation detector head assemblies, and places the cooling unit and radiation detector head assemblies in fluid communication with each other. The output flow of air from the cooling unit is delivered to the plural radiation detector head assemblies.

In accordance with another embodiment, an imaging system includes a pixelated detector and a processing unit. The pixelated detector has individually read pixels. The processing unit includes one or more processors and at least one memory comprising a tangible and non-transitory computer readable storage medium including instructions configured to instruct the one or more processors to count events detected by the detector units using a corresponding threshold and window for each pixel, wherein at least one of the threshold or the window are individually tailored for each pixel.

In accordance with another embodiment, a method includes acquiring radiation events with a pixelated detector having individually read pixels. The method also includes counting, with a processing unit comprising at least one processor, the events detected by the pixelated detector using a corresponding threshold and window for each pixel, wherein at least one of the threshold or the window are individually tailored for each pixel.

BRIEF DESCRIPTION OF THE DRAWINGS

FIG. 13 shows a schematic view of an imaging system, according to an embodiment.

DETAILED DESCRIPTION

Figure 1:
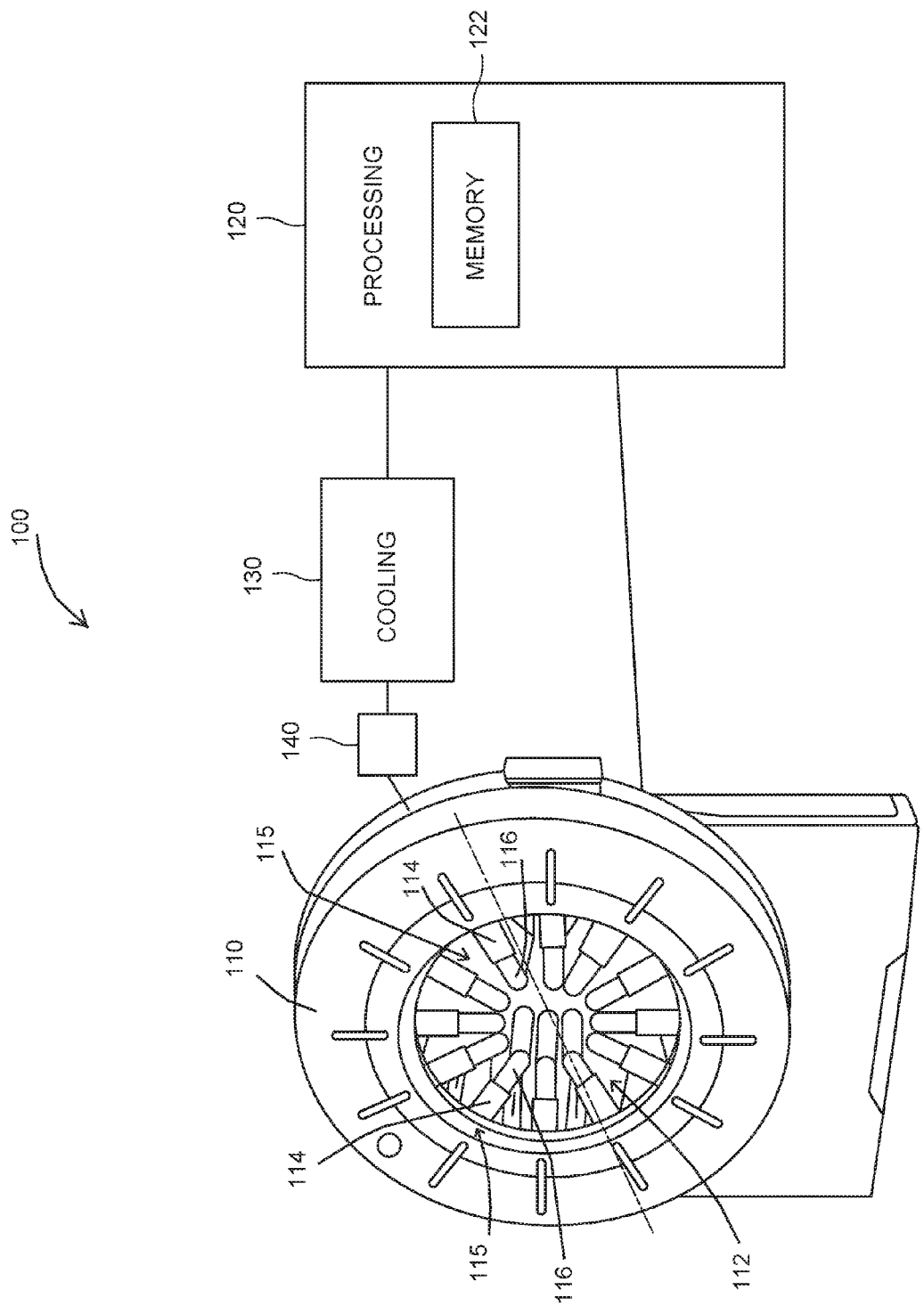
FIG. 1 provides a schematic view of a nuclear medicine (NM) multi-head imaging system according to an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or am connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide for improved control of temperature for detectors, accordingly reducing changes in detector performance due to change in temperature. Various embodiments provide controlled circulation of air (e.g., cooling air) to detectors to one or more of remove heat, remove moisture, or control temperature, thereby improving performance stability of radiation detectors. In various embodiments, a single cooling unit may be utilized for plural groups of radiation detector assemblies (e.g., plural radiation detector head assemblies distributed about the bore of a gantry of an imaging system). Air ducts (e.g., flexible pipes, hoses, or the like) may be used to distribute cold air to columns or detector head assemblies, and to return hot air to a cooling unit (or, alternatively, to exhaust hot air to an atmosphere). In some embodiments, hot air may be exhausted to an atmosphere via holes or opening in a column cover or a detector head cover. In some embodiments, each column or detector head assembly has an individual fan urging cold air from the ducts to a detector head.

In various embodiments, a threshold (and/or window setting) is individually set for each pixel (e.g., each pixel of a CZT detector). For example, the threshold may be set as low as possible while still being high enough to not compromise the ability to detect real events. The threshold, for example, may be set high enough to avoid overwhelming processing capabilities of an imaging system. A count rate for each pixel in various embodiments is monitored, and the threshold may be adjusted if appropriate. Individual tailoring of pixel threshold in various embodiments increases yield (by reducing the number of rejected pixels or detectors), and/or allows for improved detection of relatively lower energy events (e.g., charge sharing events having energy split or shared between neighboring pixels). In some embodiments, the threshold may be adjusted based on changes in temperature.

Various embodiments provide adaptive energy windows for radiation detectors (e.g., windows for counting radiation events that may be set and/or adjusted on a per pixel basis). For example, a corresponding energy window may be defined for each pixel in a pixelated detector (e.g., CZT detector). For each pixel, the energy window may be optimized to provide a trade-off between sensitivity and scatter. For example, for pixels with high energy resolution characteristics, narrow energy windows may be used. Poor performing pixels may not be turned off but may instead be downwardly weighted in a resulting image, and may be augmented by counts of neighboring pixels. In some embodiments, temperature sensors may be used to track temperature change and used to account for energy drift due to temperature change. In some embodiments, the leading edge (e.g., portion leading up to a peak) of a spectrum or signal produced by a pixel may be used to adjust energy calibration. The leading edge may be defined by a fraction or percentage of the number of counts for the energy level having the most counts.

In various embodiments, a calibration process may be performed in which, for each pixel, the energy response is measured at different temperatures, and the energy window for each pixel optimized for each temperature and application. For example, a first window for a given pixel may be defined for high sensitivity applications, and a second window for a given pixel may be defined for high resolution applications.

Various embodiments provide improved determination of the true energy response of a pixel. Knowledge of the true energy response of a pixel may be utilized for qualifying the pixel and for correctly setting an energy window for the pixel during imaging. To measure a true energy response, a pure single-peak source may be employed; however, such sources may be difficult to obtain. Cobalt, for example, has two peaks. Technetium (Tc) is a single peak isotope; however Tc sources may have internal and/or container scatter or contamination from a shield used with the Tc source. In various embodiments, the energy response of the pixel may be obtained by computing a deconvolution process with a known true spectrum of the source.

Various embodiments provide post-acquisition spectral analysis for detector systems. For example, in some embodiments, in addition to providing a diagnostic image, a list file containing all detected events during an acquisition may be saved. Additional information such as timing information (e.g., time-ticks), temperature readings, camera motion, or the like may also be saved. The information may then be utilized by one or more processors to perform post processing to produce an updated model of the detector behavior, and/or to adjust settings (e.g., threshold and/or window). By providing improved accuracy, such calibration may allow the use of narrower energy windows to provide improved imaging.

A technical effect of at least one embodiment includes improved image quality (e.g., due to improved performance stability due to reduction in temperature changes). A technical effect of at least one embodiment includes reduced cost of producing detectors (e.g., by increasing production yield). A technical effect of at least one embodiment includes reduced maintenance costs (e.g., by reducing the number of detectors to be replaced). A technical effect of at least one embodiment includes increased detector sensitivity.

FIG. 1 provides a schematic view of a nuclear medicine (NM) multi-head imaging system 100 in accordance with various embodiments. Generally, the imaging system 100 is configured to acquire imaging information (e.g., photon counts) from an object to be imaged (e.g., a human patient) that has been administered a radiopharmaceutical. The depicted imaging system 100 includes a gantry 110 having a bore 112 therethrough, plural radiation detector head assemblies 115, a cooling unit 130, a manifold 140, and a processing unit 120.

The gantry 110 defines the bore 112. The bore 112 is configured to accept an object to be imaged (e.g., a human patient or portion thereof). As seen in FIG. 1, plural radiation detector head assemblies 115 are mounted to the gantry 110. In the illustrated embodiment, each radiation detector head assembly 115 includes an arm 114 and a head 116. The arm 114 is configured to articulate the head 116 radially toward and/or away from a center of the bore 112 (and/or in other directions), and the head 116 includes at least one detector, with the head 116 disposed at a radially inward end of the arm 114 and configured to pivot to provide a range of positions from which imaging information is acquired.

The detector of the head 116, for example, may be a semiconductor detector. For example, a semiconductor detector various embodiments may be constructed using different materials, such as semiconductor materials, including Cadmium Zinc Telluride (CdZnTe), often referred to as CZT, Cadmium Telluride (CdTe), and Silicon (Si), among others. The detector may be configured for use with, for example, nuclear medicine (NM) imaging systems, positron emission tomography (PET) imaging systems, and/or single photon emission computed tomography (SPECT) imaging systems.

In various embodiments, the detector may include an array of pixelated anodes, and may generate different signals depending on the location of where a photon is absorbed in the volume of the detector under a surface if the detector. (See also FIGS. 11 and 12, and related discussion.) The volumes of the detector under the pixelated anodes are defined as voxels (not shown in FIG. 1). For each pixelated anode, the detector has a corresponding voxel. The absorption of photons by certain voxels corresponding to particular pixelated anodes results in charges generated that may be counted. The counts may be correlated to particular locations and used to reconstruct an image.

In various embodiments, each detector head assembly 115 may define a corresponding view that is oriented toward the center of the bore 112. Each detector head assembly 115 in the illustrated embodiment is configured to acquire imaging information over a sweep range corresponding to the view of the given detector unit. Additional details regarding examples of systems with detector units disposed radially around a bore may be found in U.S. patent application Ser. No. 14/788,180, filed 30 Jun. 2015, entitled "Systems and Methods For Dynamic Scanning With Multi-Head Camera," the subject matter of which is incorporated by reference in its entirety.

The processing unit 120 includes memory 122. The imaging system 100 is shown as including a single processing unit 120; however, the block for the processing unit 120 may be understood as representing one or more processors that may be distributed or remote from each other. The depicted processing unit 132 includes processing circuitry configured to perform one or more tasks, functions, or steps discussed herein. It may be noted that "processing unit" as used herein is not intended to necessarily be limited to a single processor or computer. For example, the processing unit 120 may include multiple processors and/or computers, which may be integrated in a common housing or unit, or which may distributed among various units or housings.

Generally, various aspects (e.g., programmed modules) of the processing unit 120 act individually or cooperatively with other aspects to perform one or more aspects of the methods, steps, or processes discussed herein (e.g., method 1200 or aspects thereof). In the depicted embodiment, the memory 122 includes a tangible, non-transitory computer readable medium having stored thereon instructions for performing one or more aspects of the methods, steps, or processes discussed herein.

Figure 2:
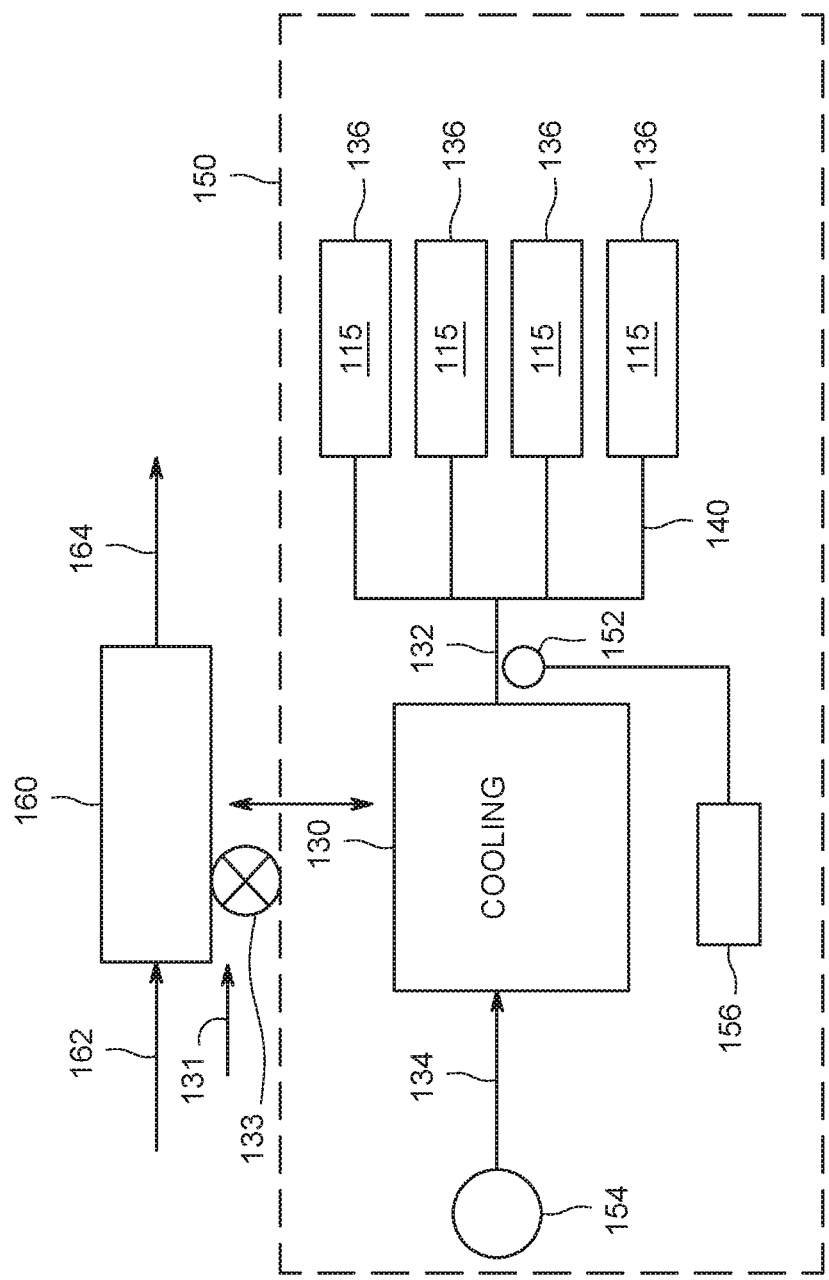
FIG. 2 provides a schematic view of the system of FIG. 1 in an open loop arrangement.

As mentioned above the imaging system 100 also includes a cooling unit 130 and a manifold 140. FIG. 2 illustrates a schematic view of the imaging system 100 including the cooling unit 130 and manifold 140. The cooling unit 130 in various embodiments is mounted to the gantry 110 (e.g., mounted proximate to an interior cavity or housing within the gantry 110). Generally, the cooling unit 130 is configured to provide an output flow 132 of air at a controlled temperature. The output flow 132 is provided to the detector head assemblies 115, for example to cool or stabilize temperatures of detector electronics, as the electronics tend to heat up as they are activated or used. In some embodiments, the cooling unit 130 may be a thermoelectric chiller (TEC).

As schematically depicted in FIG. 2, the manifold 140 is coupled to the cooling unit 130 and to the radiation detector head assemblies 115. For example, the manifold 140 may include one or more of pipes, tubes, hoses, or ducting, for example, that define a fluid pathway between the cooling unit 130 and the radiation detector head assemblies 115. The depicted manifold 140 places the cooling unit 130 in fluid communication with the radiation detector head assemblies 115. As seen in FIG. 2, the output flow 132 of air from the cooling unit 130 is delivered to the radiation detector head assemblies 115. By using one cooling unit 130 for all of the radiation detector head assemblies 115, consistency of control of air temperature for air provided to the radiation detector head assemblies may be improved, and/or cost for the imaging system 100 may be reduced by using only one cooling unit 130 instead of separate cooling units mounted on each radiation detector head assembly 115. Accordingly, in some embodiments, only a single cooling unit 130 may be used for all of the radiation detector head assemblies 115 of the system 100. In other embodiments, more than one cooling unit 130 may be employed (e.g., with each cooling unit contributed to an output flow shared among the radiation detector head assemblies, or with each cooling unit providing an output flow to a dedicated group of the radiation detector head assemblies).

It may be noted that the distribution of air for the imaging system 100 may be configured as an open loop distribution or a closed loop distribution. FIG. 2 illustrates the imaging system 100 in an open loop air distribution configuration. In FIG. 2, the cooling unit 130 receives an inlet flow 134 from an atmospheric source. A fan 154 in the illustrated embodiment is used to provide the inlet flow 134 to the cooling unit 130 for distribution amount the radiation detector head assemblies 115. In some embodiments, the atmospheric source may be located in the same room or immediate environment as the gantry 110. In some embodiments, the atmospheric source may be located remotely (e.g., in a different room) from the gantry 110, for example to reduce any potential airborne contamination that may enter the air flow. After the output flow 132 is distributed to the radiation detector head assemblies 115 and used to cool the radiation detector head assemblies 115, an exhaust flow 136 is routed away from the radiation detector head assemblies 115. For control of the cooling unit 130, fan 154, and/or other aspects of the system 100, a temperature sensor 152 senses temperature of the output flow 132 and provides temperature information to a temperature controller 156. Additional or alternative temperature sensors may be used to sense temperatures of other flows, such as the inlet flow 134 and/or the exhaust flow 136.

As seen in FIG. 2, the cooling unit 130 may be considered as a cold side of a heat exchange interface 131 (which may include a heat pump 133), that cooperates with heat exchanger 160 to remove heat from the cooling unit 130. The heat exchanger 160 may receive a flow 162 of room air in which is heated in the heat exchanger 160 and exhausted as a heated flow 164 of room air out. Accordingly, heat removed from the radiation detector head assemblies 115 may be removed from an enclosure 150 surrounding the detection components and/or gantry of the system 100, with the heat transferred to an atmosphere outside of the enclosure 150 via the heat exchanger 160.

Figure 3:
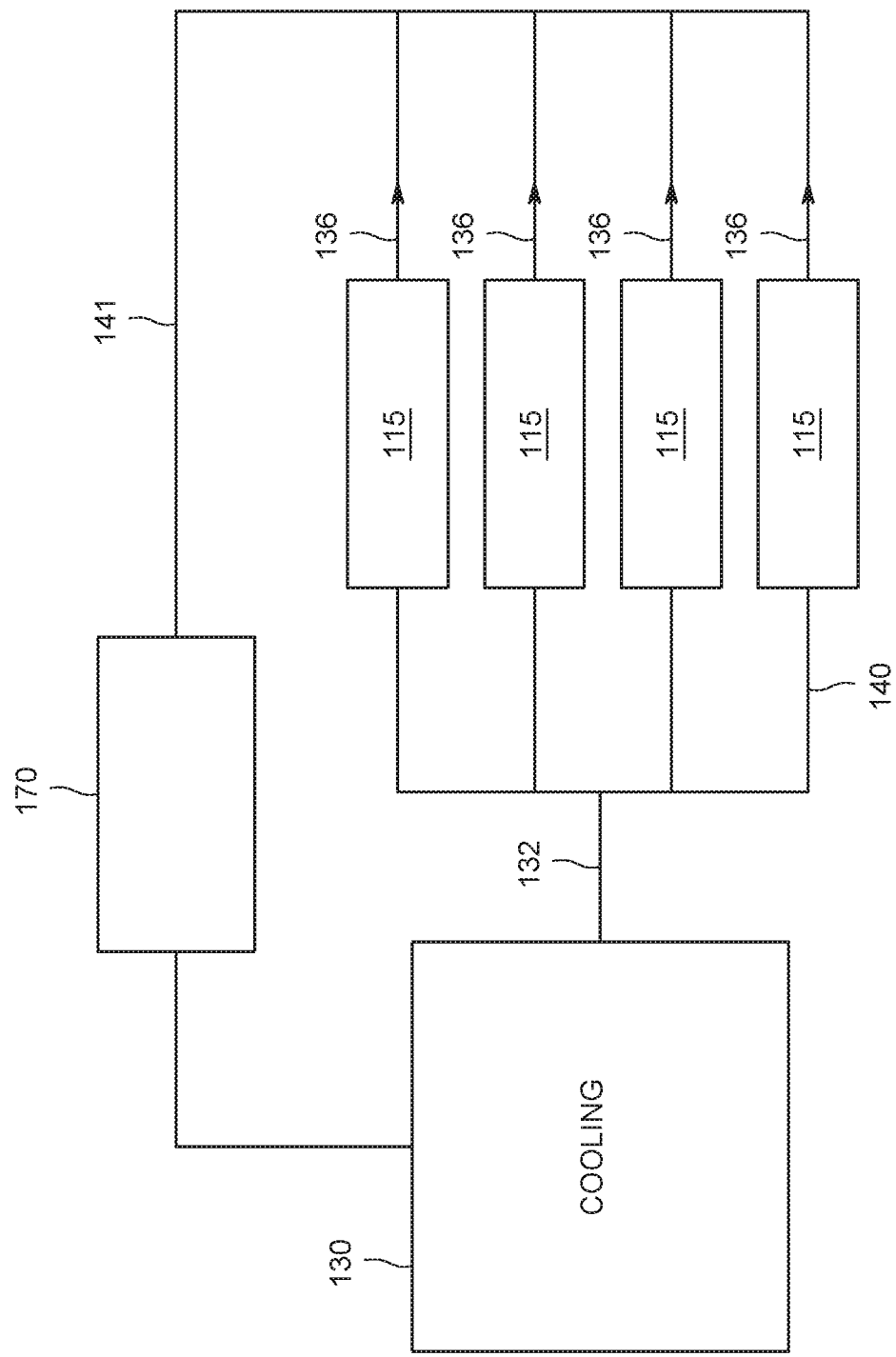
FIG. 3 provides a schematic view of the system of FIG. 1 in a closed loop arrangement.

FIG. 3 illustrates the imaging system 100 in a closed loop air distribution configuration. In FIG. 3, after the output flow 132 is distributed to the radiation detector head assemblies 115 and used to cool the radiation detector head assemblies 115, the exhaust flow 136 is routed away from the radiation detector head assemblies 115 to the cooling unit 130 via an exhaust manifold 141. The example system depicted in FIG. 3 also includes a dessicator 170 configured to remove moisture from the exhaust flow 136 as it is returned to the cooling unit 130. It may further be noted that, while not depicted in FIG. 3 for ease and clarity of depiction, the system of FIG. 3 may include generally similar components for heat exchange and temperature control as discussed in connection with the example of FIG. 2.

Figure 4:
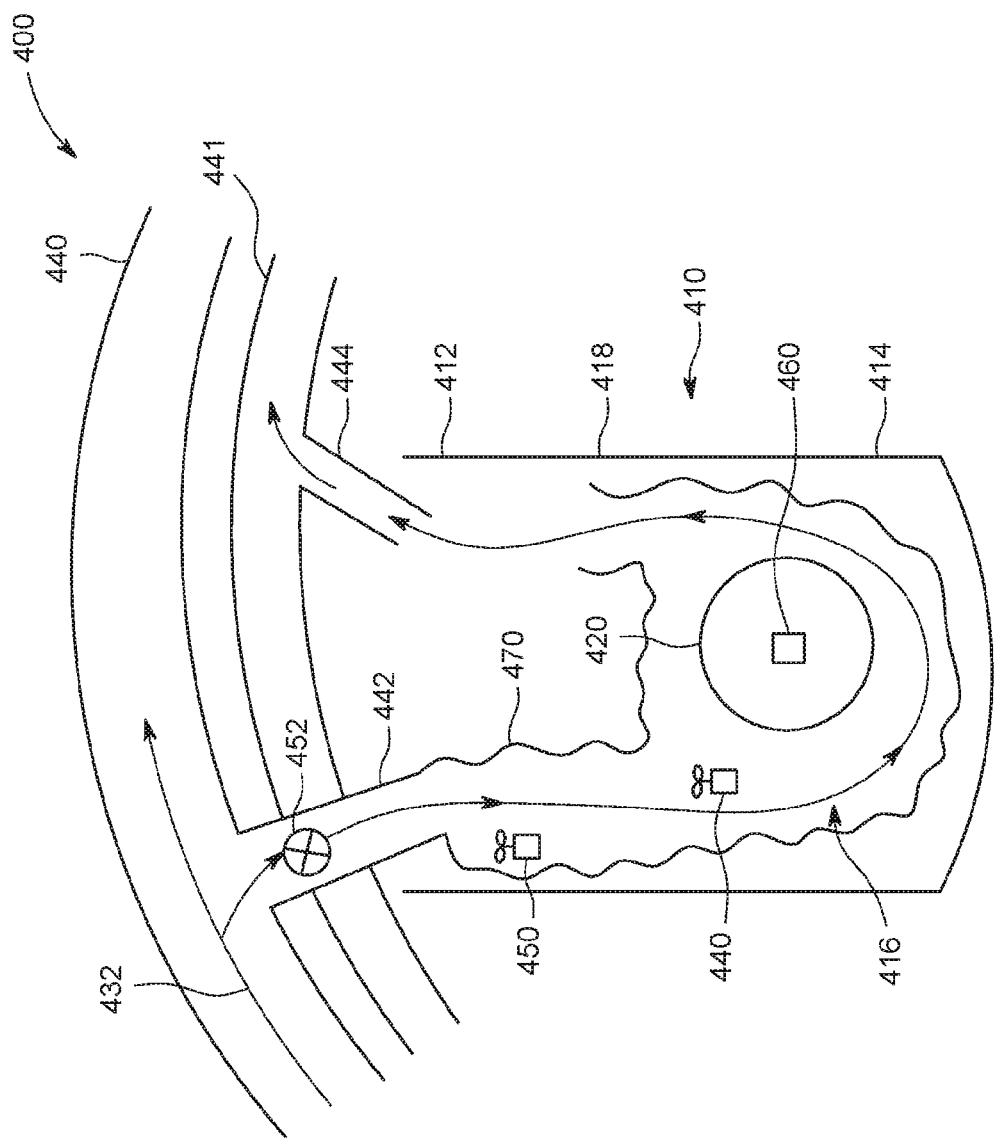
FIG. 4 illustrates a schematic view of an air circulation system according to an embodiment.

FIG. 4 illustrates a schematic view of an air circulation system 400 for an imaging system (e.g., imaging system 100). Only one radiation detector head assembly is shown in FIG. 4 for clarity and ease of illustration; however, similar arrangements may be provided for plural radiation detector head assemblies of a given imaging system. As seen in FIG. 4, a radiation detector head assembly 410 includes an arm 412 and a head 414. A passageway 416 is defined between a housing 418 and a rotor assembly 420. A detector unit (not shown in FIG. 4) is disposed within the rotor assembly 420. As seen in FIG. 4, a cooling flow 432 of cooling air (e.g., from cooling unit 130) travels through a cooling manifold 440. An inlet 442 places the cooling manifold 440 in fluid communication with the passageway 416 of the radiation detector head assembly 410. Accordingly, air from the cooling flow 432 may be diverted from the cooling manifold 440 to the passageway 416 and used to cool the rotor assembly 420 (e.g., an electronic detector within the rotor assembly 420). A fan 450 in the illustrated embodiment helps direct the air in a desired direction through the passageway 416, while a valve 452 is used to control an amount of air diverted from the cooling manifold 440 to the passageway 416. Additionally or alternatively, in some embodiments, a fan 490 assists or causes air flow into the rotor assembly 420. Optionally, each fan 490 may be controlled to vary the volume of air through the rotor assembly 420 it serves in order to control and stabilize the temperature in the rotor assembly 420 it serves. After the air has passed and cooled the rotor assembly 420, the air is directed via the passageway to an outlet 444, which is in fluid communication with an exhaust manifold 441. The exhaust manifold 441 may be configured to route air back to a cooling source (e.g., cooling unit 130) in a closed air distribution configuration, or may be configured to route exhausted air to an atmosphere in an open air distribution configuration. The cooling manifold 440 and the exhaust manifold 441, for example, may be disposed within a gantry (e.g., gantry 110). It may be noted that one or more aspects of the air circulation system 400 (e.g., inlet 442 and/or outlet 444) may be configured to allow for extension and/or retraction of the arm 412 to translate the head 414 radially within a bore of a gantry. For example, the inlet 442 and/or outlet 444 may include a length of flexible hose. In the illustrated embodiment, a flexible hose 470 extends from the inlet 442 to an air inlet of the rotor assembly 420 to direct cooling air to electronics of the radiation detector head assembly 410. Optionally, a generally similar flexible hose (not shown in FIG. 4) may extend from an exhaust outlet of the rotor assembly 420 to direct spent cooling air to the exhaust manifold 441. Flexibility of the air hose accounts for the radial motion of rotor assembly 420 respective to the gantry. Directing air from the cooling manifold 440 through the rotor assembly 420 to the exhaust manifold 441 helps provide efficient cooling.

Figure 14B:
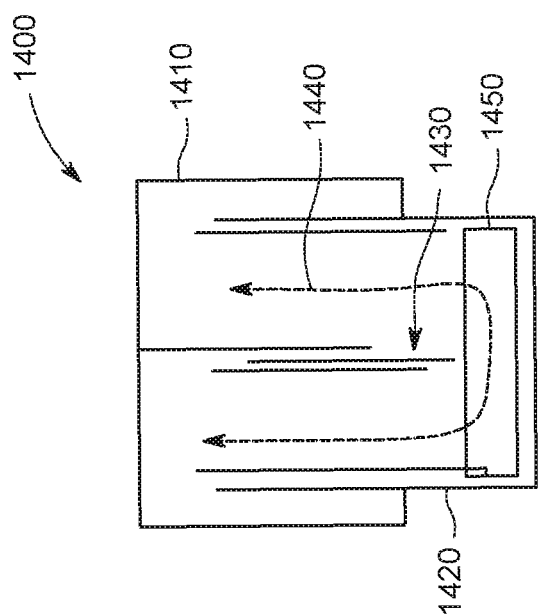
FIG. 14b depicts the telescoping assembly of FIG. 14a in a retracted position.
Figure 14A:
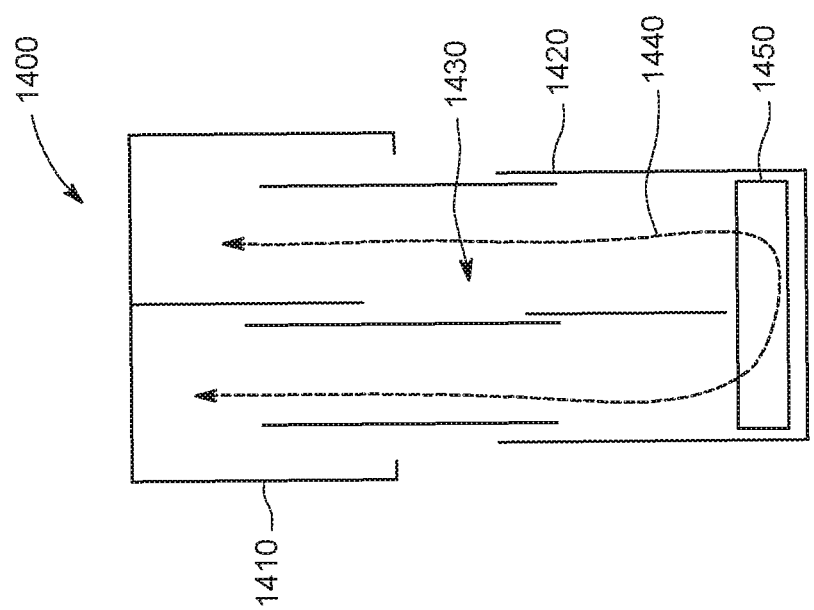
FIG. 14a depicts a telescoping assembly in an extended position, accordingly to an embodiment.

Alternatively or additionally, a telescoping baffle arrangement may be used to direct air to the electronics of the radiation detector head assembly while permitting the detector head assembly to articulate radially inwardly and outwardly. FIG. 14a depicts a telescoping assembly 1400 in an extended position and FIG. 14b depicts the telescoping assembly 1400 in a retracted position. In FIGS. 14a and 14b, the telescoping assembly 1400 is shown along an axial cross-section. The telescoping assembly includes an arm 1410 with a telescoping arm portion 1420. The telescoping assembly 1410 also includes a telescoping septum 1430 that divides the telescoping assembly 1400 and defines a passageway through which cooling air flow 1440 may pass through the interior of the telescoping assembly 1400 to cool detector electronics 1450. In such a way, the lumen in the gantry is divided to a cooling manifold (generally equivalent to 440 in FIG. 4) and exhaust manifold (generally equivalent to 441 in FIG. 4), respectively, open to the two lumens on each side of the telescoping septum 1430. Accordingly, cooling air may be forced to traverse the detector electronics 1450.

As also discussed herein, in various embodiments, one or more signal processing characteristics of a detector (e.g., individual pixels of a detector), such as a window or threshold (see, e.g., FIG. 11 and related discussion) may be varied based on temperature. The depicted air circulation system 400 includes a temperature sensor 460 operably coupled to a processing unit (e.g., processing unit 120) and configured to provide temperature information to the processing unit. Using the temperature information, the processing unit 120 may adjust the one or more signal processing characteristics. Accordingly, even if detected energy values detected by the detector drift due to temperature variation, the drift may be addressed to provide improved reliability and accuracy. It may be noted that the number and/or position of the temperature sensor 460 may differ in various embodiments. For example, a single temperature sensor 460 may be used for an entire system in some embodiments. In other embodiments, each radiation detector head assembly may have a dedicated temperature sensor used to provided temperature information used by the processing unit to adjust signal processing characteristics of pixels of detectors disposed on a corresponding detector head. Accordingly, pixels of detectors on different detector heads may be adjusted based on the particular temperature of the particular detector head on which they are disposed. Temperature sensors in various embodiments may be used to sense temperature of air surrounding a detector, temperature of air in a cooling flow, temperature of air in an exhaust flow, and/or temperature of detector electronics (e.g., using a thermistor).

Figure 5:
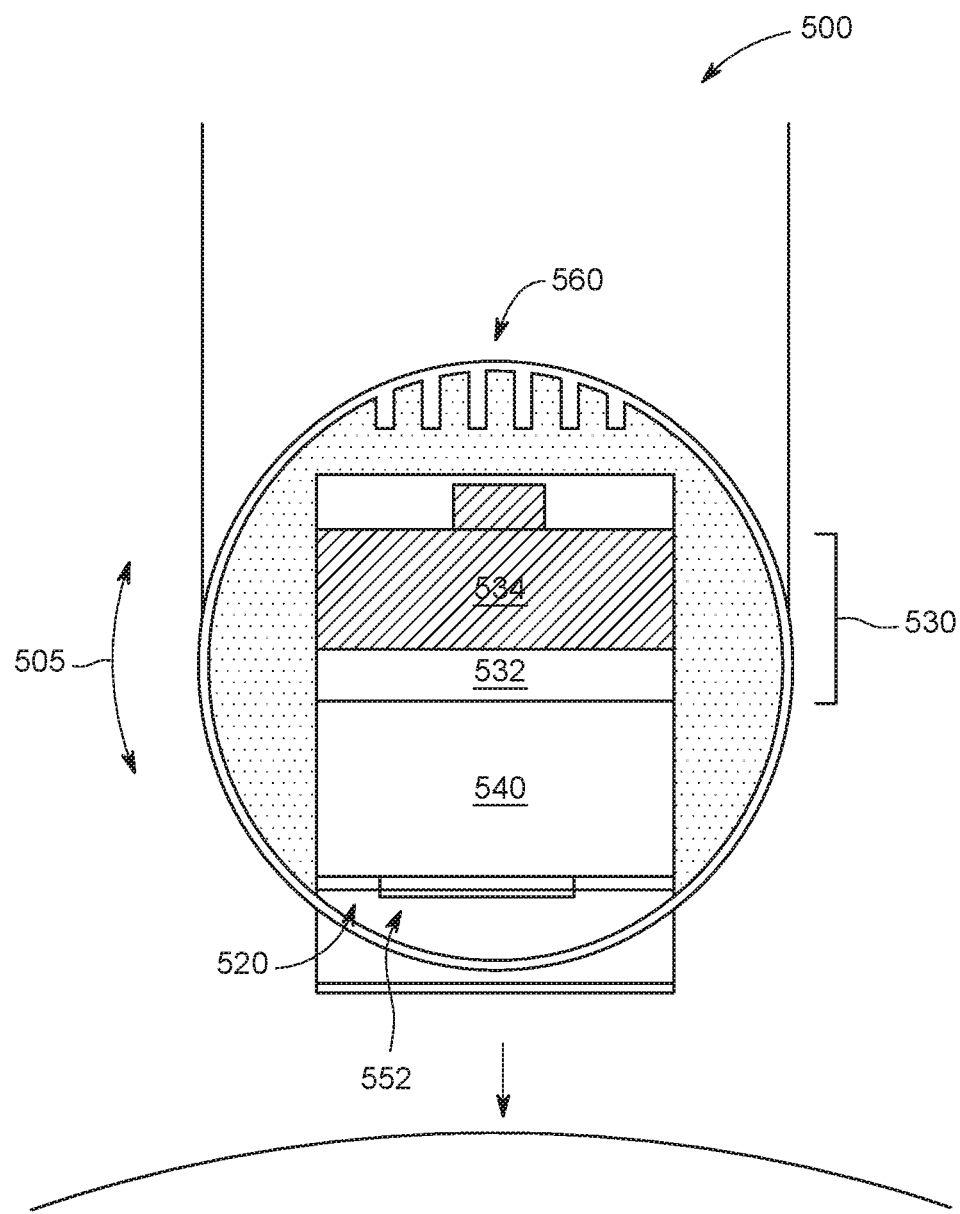
FIG. 5 provides a sectional schematic view of a radiation detector head assembly according to an embodiment.

FIG. 5 provides a sectional schematic view of a radiation detector head assembly 500 in accordance with various embodiments. One or more aspects of the radiation detector head assembly 500 may be employed in connection with one or more of the radiation detector head assemblies 115 of the example discussed in connection with FIG. 1. Additional details of example radiation detector head assemblies may be found at U.S. patent application Ser. No. 14/671,039, "Reduced Airborne Contamination Detector Heads," filed Mar. 27, 2015, the subject matter of which is hereby incorporated in its entirety. It may be noted that the radiation detector head assembly 500 may be utilized in connection with medical imaging (e.g., nuclear medicine (NM) imaging, positron emission tomography (PET), single photon emission computed tomography (SPECT), or the like). For example, the radiation detector head assembly 500 may be a portion of an imaging system configured to image an object 502 (or a portion thereof). The object 502, for example, may be a human patient. In the illustrated embodiment, the radiation detector head assembly 500 includes an arm 513 that may adjustably couple the radiation detector head assembly 500 to a gantry (not shown in FIG. 5; see FIG. 1 for an example of a gantry) of an imaging system. The radiation detector head assembly 500 in various embodiments is one of a group of assemblies that each define smaller individual fields of view that may be combined to provide a larger, combined field of view of an object being imaged. For example, the radiation detector head assembly 500 may be generally cylindrically shaped with a diameter of about 2.5 inches and a length of about 14 inches.

In the illustrated embodiment, the depicted radiation detector head assembly 500 includes a detector housing 510 and a rotor assembly 520. The rotor assembly 520 is disposed within the detector housing 510 and is configured to be rotated in a rotational direction 505 about an axis. Rotation of the rotor assembly 520 may be performed to orient a detector with the rotor assembly in a desired orientation with respect to the object 502 being imaged.

As seen in FIG. 5, the depicted detector housing 510 defines a cavity 512 therein, with the rotor assembly 520 disposed within the cavity 512. The depicted detector housing 512 includes a detector cover 516 (within which the cavity 512 is defined) and an arm cover 514 for an arm 513 used to articulate the radiation detector assembly 510 relative to a gantry (not shown in FIG. 5) or other structure to which the radiation detector assembly 500 is mounted via the arm 513. All or a portion of the detector housing 510 may be made from a light, strong material that is generally transparent to radiation emitted from an object being imaged, such as carbon fiber. All or a portion of the detector housing 510 may include a metal lining or other structure configured to address, reduce, or eliminate electromagnetic interference (EMI).

The depicted rotor assembly 520 includes a detector unit 530, a collimator 540, a body 550, and a sealing member 542. Other arrangements include additional or alternative components may be employed in various embodiments. Generally, the detector unit 530 is configured to detect radiation emitted from the object 502 (e.g., a human patient). The collimator 540 is interposed between the detector unit 530 and the object 502, and is configured to control angles at which radiation is allowed to pass to the detector unit 530 from the object 502 in an imaging direction 504. For example, the collimator 540 in some embodiments includes an array of tubes having small diameter holes configured to allow passage of photons only in a generally normal direction to a detector surface of the detector unit 530. The detector unit 530 includes an absorption member 532 and associated processing circuitry 534. Generally, the absorption member 532 is configured to receive radiation passing through the collimator 540 and to generate electronic signals, in conjunction with the processing circuitry 534, in response to radiation received and/or absorbed by the absorption member 532. The absorption member 532 may be formed of a semiconductor material, such as Cadmium Zinc Telluride (CdZnTe), often referred to as CZT, Cadmium Telluride (CdTe), or Silicon (Si), among others. In the illustrated embodiment, the body 550 is configured as, and may also be understood as, a radiation shielding unit. For example, the body 550 partially surrounds the detector unit 530, and is configured of a material (e.g., Lead or Tungsten, among others) that blocks, limits, inhibits, and/or prevents the passage of radiation emitted from the object 502 therethrough. An opening 552 is defined by the body 550 and generally oriented in the imaging direction 504 allowing the passage of radiation emitted from the object 502 to pass on to the collimator 540 and the detector unit 530. Generally, in the illustrated embodiment, the body 550 acts to block radiation from entering the absorption member 532 from any orientation or direction other than via the collimator 540.

It may be noted that, in use, the processing circuitry 534 may generate an amount of heat that can potentially affect performance of the detector unit 530. Accordingly, air (e.g., from the cooling unit 130) may be directed over the rotor assembly 520 including the detector unit 530 to cool the detector unit 530, to provide temperature stabilization to the detector unit 530, and to prevent or inhibit loss of performance due to heating of the detector unit 530. In the illustrated embodiment, the body 550 (within which the collimator 540 and detector unit 530 are disposed) is spaced at a distance from an interior surface of the detector housing 510, thereby defining a passageway 554. The passageway 554 extends circumferentially around the rotor assembly 520 (e.g., around the body 150) and also extends axially or along the length of the rotor assembly 520 and body 550. The passageway 554 in various embodiments is in fluid communication with a cooling manifold (e.g., manifold 140) and receives cooling air via the cooling manifold from a cooling unit (e.g., cooling unit 130). The passageway 554 allows for the passage of air (e.g., axially) over the body 550 as well as providing a clearance for rotational movement of the rotor assembly 520 with respect to the detector housing 510. For example, air may be passed over the rotor assembly 520 axially (e.g., in a direction along the length or axis of the rotor assembly 520, or into and/or out of the page of FIG. 5) and/or transversely (in a direction transverse to the axis such as clockwise or counterclockwise around a cross-section of the rotor assembly 120).

As seen in FIG. 5, the body 550 partially surrounds the detector unit 530, and includes the opening 552 to allow the passage of radiation emitted from the object 502 to pass on to the collimator 540 and the detector unit 530. Generally, the body 550 acts to block radiation from entering the absorption member 532 from any orientation or direction other than via the collimator 540. In the illustrated embodiment, the body 550 comprises a shielding member 556 that is surrounded by a casing 558. For example, the shielding member 556 may be formed of a radiation blocking material such as Lead or Tungsten, while the casing 558 may be formed of a heat conducting material such as Aluminum. Aluminum provides for conduction of heat away from the center of the rotor assembly 510 and heat exchange with cooling air passing through the passageway 554, while also being relatively lightweight and providing sufficient structural strength for the rotor assembly 520 to maintain its shape during rotation. In the illustrated embodiment, the casing 558 completely surrounds the shielding member 556, with the shielding member completely contained within an interior of the casing 558.

In the illustrated example of FIG. 5, the casing 558 of the body 550 includes fins 560 formed along an exterior surface 559 of the casing. The fins 560 may extend along all of the length of the body 550 or a portion thereof. The depicted fins 560 define openings extending into the body 550, allowing for increased surface area for improved heat exchange between the casing 558 and a cooling air flow while still allowing a generally circular cross-section for the rotor assembly 520 for interference free rotation within the detector housing 510 without requiring an overly large gap between the rotor assembly 520 and the detector housing 510. In the example of FIG. 5, the fins 560 extend axially along an exterior of the rotor assembly 510, with the depicted fins 560 extending axially along the exterior surface 559 of the casing 558.

It may be noted that in the embodiment depicted in FIG. 5, a passageway providing cooling airflow is provided directly around the rotor assembly. Alternatively, in various embodiments, a passageway providing a cooling airflow to a rotor assembly may be enclosed from the rotor assembly, and be utilized for heat exchange with a second passageway surrounding the rotor assembly.

Figure 6:
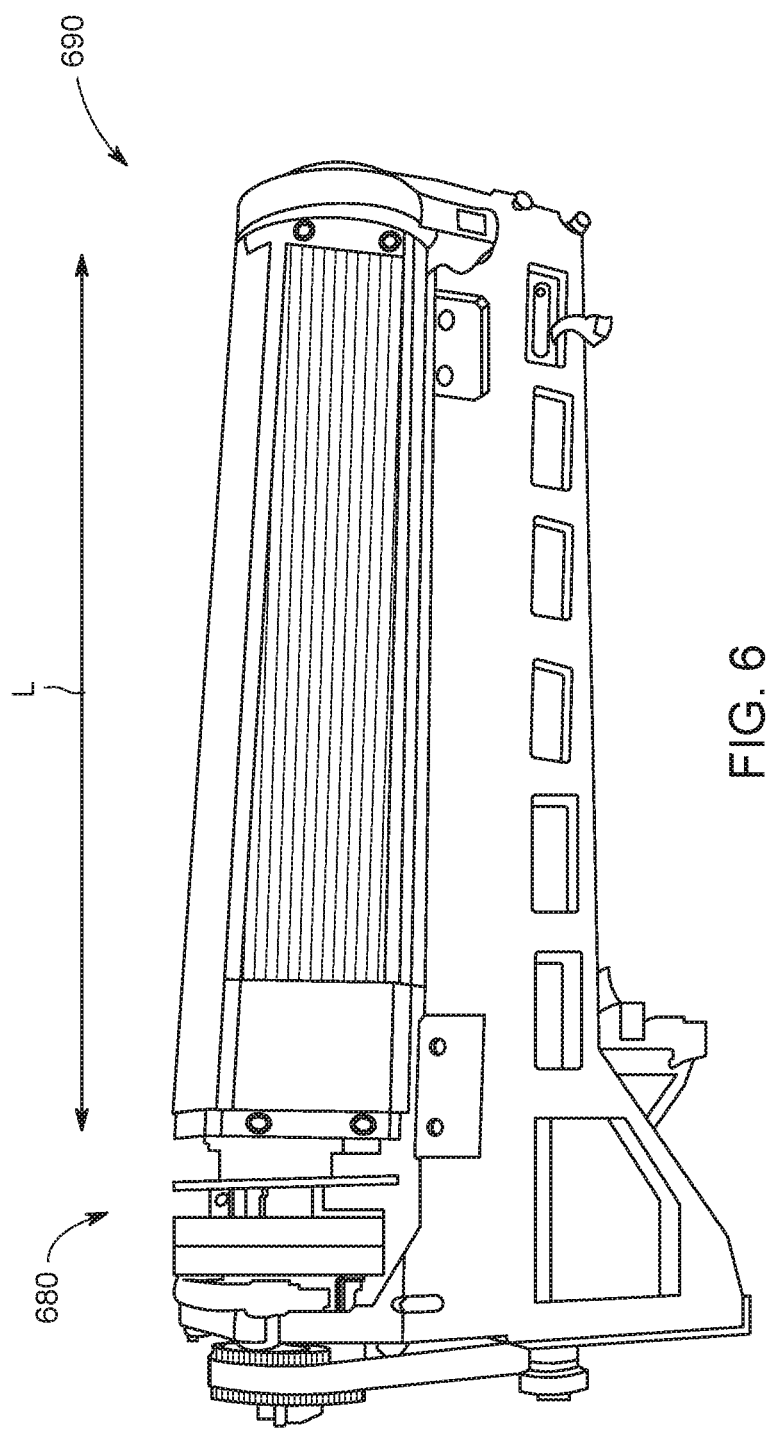
FIG. 6 provides a side view of a radiation detector head assembly according to an embodiment.

As discussed herein, disposed cooling air flow may be passed axially or over the length of a radiation detector head assembly. FIG. 6 shows a side view of a radiation detector head assembly 600, including a motor for rotating the rotor assembly within the housing, which may also be referred to as pivoting the radiation detector head assembly, formed in accordance with various embodiments. As seen in FIG. 6, the depicted radiation detector head assembly 600 includes a motor 610, a pivot belt 612, a slip-ring 614, electronics module 616, a rotor 618, a stator 620, a collimator 622, and an air duct 624. A cover or housing for the radiation detector head assembly 600 has been removed for improved clarity and ease of illustration. As also seen in FIG. 6, a length L extends along the radiation detector head assembly from a first end 680 to a second end 690. Cooling air may be provided to the radiation detector head assembly 600 initially at the first end 680 (e.g., via an intake from a cooling manifold such as manifold 140), with the air becoming heated as the air passes along the length L to the second end 690.

The motor 610 (e.g., an electric motor) may be controlled by a processing unit of an imaging system to rotate the rotor 618 (which may include one or more aspects of rotor assemblies discussed herein). The motor 610 is mounted to the stator 620, and is coupled to the rotor 618 via the pivot belt 612. The slip-ring 614 allows for electrical communication between the electronics module 616 (which rotates with the rotor 618) and electronics mounted to the stator 620 or other structure that does not rotate with the rotor 618. In some embodiments, the rotor 618 may rotate over a range of; for example, about 210 degrees to provide flexibility in orienting a detector of the radiation detector head assembly 600. The air duct 624 is in fluid communication with a passageway surrounding at least a portion of the rotor 618 to provide for heat removal from the rotor 618 (e.g., using air from the cooling unit 130). Additional discussion regarding example system including radiation detector head assemblies may be found in U.S. patent application Ser. No. 14/016,939, filed Sep. 3, 2013, entitled "Methods And Systems For Controlling Movement Of Detectors Having Multiple Detector Heads," which is hereby incorporated by reference in its entirety.

As discussed above, fins may be used to improve heat transfer between a radiation detector head assembly (e.g., radiation detector head assembly 115) and a cooling flow of air. It may be noted that in various embodiments, the fins may extend from an exterior surface of a casing of a rotor assembly, with the fins configured to have variable heat transfer capability along a length of the rotor assembly. For example, where cooling air initially encounters the radiation detector head assembly at a first end and is heated as it travels toward a second end, the detector units of the detector head assembly may have different temperatures along the length, resulting in potentially inconsistent performance. Accordingly, the heat transfer capabilities of the fins may be relatively reduced at the first and relatively increased toward the second end, to provide for more even heat transfer along the length and accordingly more consistent temperature along the length.

Figure 7:
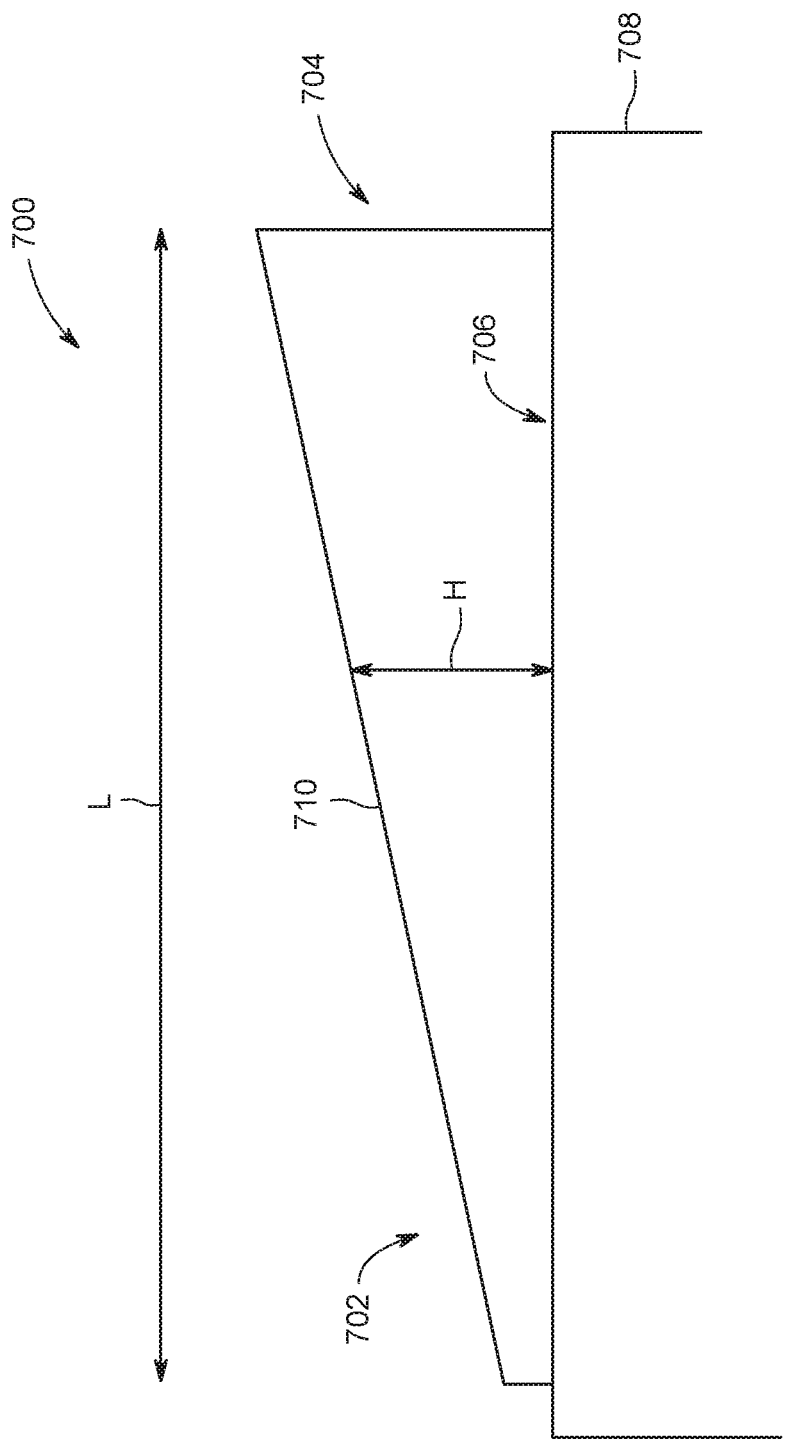
FIG. 7 depicts a side schematic view of fins according to an embodiment.

FIG. 7 depicts a side view of fins that may be used in accordance with various embodiments. As seen in FIG. 7, a rotor assembly 700 includes a fin 710 (plural fins may be distributed about a portion of a casing; however only one fin 710 is shown in FIG. 7 for case and clarity of illustration) that extends along a length L of the rotor assembly 700 from a first end 702 toward a second end 704. In the illustrated embodiments, cooling air is received initially proximate the first end 702, travels along the length L toward the second and, becoming heated (by removing heat from the rotor assembly 700) as it travels toward the second end 704. Accordingly, detector units positioned proximate the second end 704 tend to be at a higher temperature than those proximate the first end 702. By providing for increased heat transfer proximate the second end 704 and/or reduced heat transfer proximate the first end 702, more consistent or uniform temperature may be provided to the various detectors of the rotor assembly 700 disposed at different position along the length L.

In the example depicted in FIG. 7, variability of heat transfer capability is provided via variability in height of fins 710 along the length L of the rotor assembly 700. As seen in FIG. 7, the fin 710 extends from an exterior surface 706 of a casing 708 of the rotor assembly 700. The fin 710 has a variable height H that is smaller proximate the first end 702 (where a cooling air flow has a relatively lower temperature), with the variable height H larger proximate the second end 704 (where the cooling air flow has a relatively higher temperature). Accordingly, the fin 710 has greater heat transfer capability proximate the second end 704 relative to the first end 702 to provide for a more consistent or uniform temperature along the length L.

Figure 8:
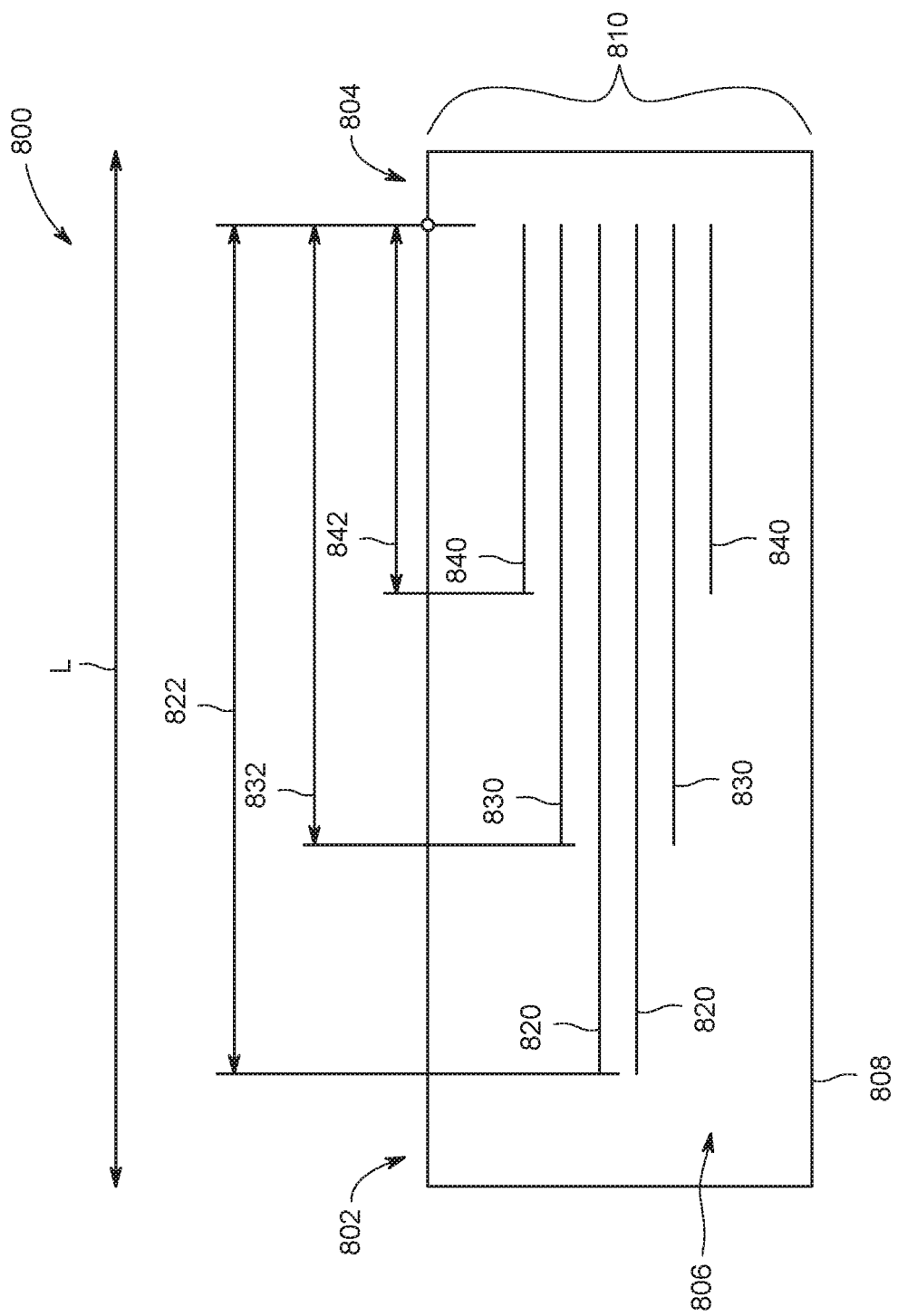
FIG. 8 depicts a schematic view of fins according to another embodiment.

Alternatively or additionally, fins may have differing fin lengths, wherein the number of fins (e.g., the number of fins at a given position along the length of the rotor assembly) varies along the length of the rotor assembly. FIG. 8 depicts an overhead view of another example of fins that may be used in various embodiments. As seen in FIG. 8, a rotor assembly 800 includes fins 810 that extend along a length L of the rotor assembly 800 from a first end 802 toward a second end 804. In the illustrated embodiments, cooling air is received initially proximate the first end 802, travels along the length L toward the second end, becoming heated (by removing heat from the rotor assembly 800) as it travels toward the second end 804. Accordingly, detector units positioned proximate the second end 804 tend to be at a higher temperature than those proximate the first end 802.

By providing for increased heat transfer proximate the second end 804 and/or reduced heat transfer proximate the first end 802, more consistent or uniform temperature may be provided to the various detectors of the rotor assembly 800 disposed at different position along the length L.

In the example depicted in FIG. 8, variability of heat transfer capability is provided via variability in the number of fins along the length L of the rotor assembly 800. The fins 810 extend from an exterior surface 806 of a casing 808 of the rotor assembly 800. As seen in FIG. 8, the fins 810 include a first group 820 having a first fin length 822 that extends along all or most of the length L; a second group 830 having a second fin length 832 that is less than the first fin length 822; and a third group 840 having a third fin length 842 that is less than the second fin length 832. The groups of fins are arranged such that the shorter fins are disposed proximate the second end 804. Accordingly, positions along the length L proximate the second end 804 tend to have more fins than positions along the length L proximate the first end 804. For example, 2 fins are present at or near the first end 802 while six fins are present at or near the second end 804. Accordingly, the fins 810 provide greater heat transfer capability proximate the second end 804 relative to the first end 802 to provide for a more consistent or uniform temperature along the length L.

Figure 9:
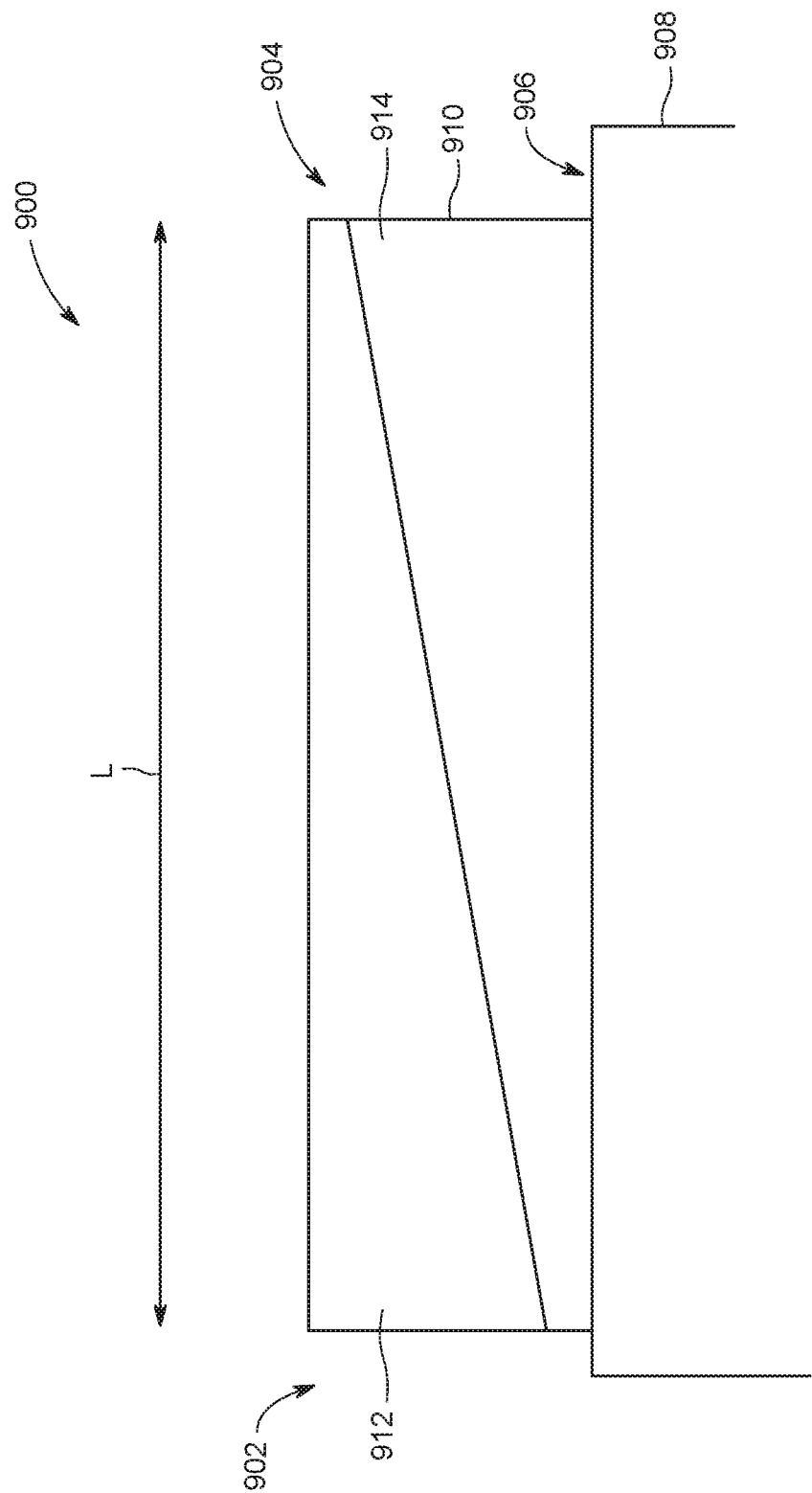
FIG. 9 depicts a side schematic view of fins according to an embodiment.

Alternatively or additionally, fins may have a variable conductivity along the length of the rotor assembly. FIG. 9 provides a side view of another example of a fin that may be used in various embodiments. As seen in FIG. 9, a rotor assembly 900 includes a fin 910 (plural fins may be distributed about a portion of a casing; however only one fin 910 is shown in FIG. 9 for case and clarity of illustration) that extends along a length L of the rotor assembly 900 from a first end 902 toward a second end 904. In the illustrated embodiments, cooling air is received initially proximate the first end 902, travels along the length L toward the second end, becoming heated (by removing heat from the rotor assembly 900) as it travels toward the second end 904. Accordingly, detector units positioned proximate the second end 904 tend to be at a higher temperature than those proximate the first end 902. By providing for increased heat transfer proximate the second end 904 and/or reduced heat transfer proximate the first end 902, more consistent or uniform temperature may be provided to the various detectors of the rotor assembly 900 disposed at different position along the length L.

In the example depicted in FIG. 9, variability of heat transfer capability is provided via variability in thermal conductivity of fins 910 along the length L of the rotor assembly 900. As seen in FIG. 9, the fin 910 extends from an exterior surface 906 of a casing 908 of the rotor assembly 900. The fin 910 has a variable thermal conductivity that is lower proximate the first end 902 (where a cooling air flow has a relatively lower temperature), and that is higher proximate the second end 804 (where the cooling air flow has a relatively higher temperature). The variable conductivity in the illustrated embodiment is provided by the use of different materials to construct the fin 910. In the illustrated embodiment, the fin 910 includes a first portion 912 of a first material having a relatively lower thermal conductivity, and a second portion 914 of a second material having a relatively higher thermal conductivity. The proportion of the first material comprising the fin 910 to the second material becomes lower along the length L as distance from the first end 902 increases (and, similarly, the proportion of the second material comprising the fin 910 becomes higher along the length L as distance from the first end 902 increases). The thermal conductivity of the fin 910 accordingly increases along the length L toward the second end 904, as the second material has a higher thermal conductivity than the first material. Accordingly, the fin 910 has greater beat transfer capability proximate the second end 904 relative to the first end 902 to provide for a more consistent or uniform temperature along the length L.

It may be noted that, as temperature varies (and/or for other reasons) the performance of the detectors may vary. For example, the energy detected by a detector may change as the temperature of the detector (e.g., the temperature of CZT in the detector) varies. Accordingly, in various embodiments, additionally or alternatively to the aspects discussed above, for example, in connection with maintaining temperature proximate a detector within a desired range, potential variance of detector performance may also be addressed. As performance may vary on a per pixel basis, in various embodiments signals from a detector are analyzed on a per pixel basis. For example, each pixel may be calibrated so that information from each pixel is addressed with individually tailored signal processing characteristics for the particular pixel. For example, a corresponding window and threshold may be used to read and count events for each pixel, with at least one of the window or threshold tailored for the individual pixel. Further still, as discussed below, the at least one of the window or threshold for individual pixels may be adjusted during imaging or over another time period (e.g., to address changes in detector performance over time and/or to address changes in temperature).

Figure 10:
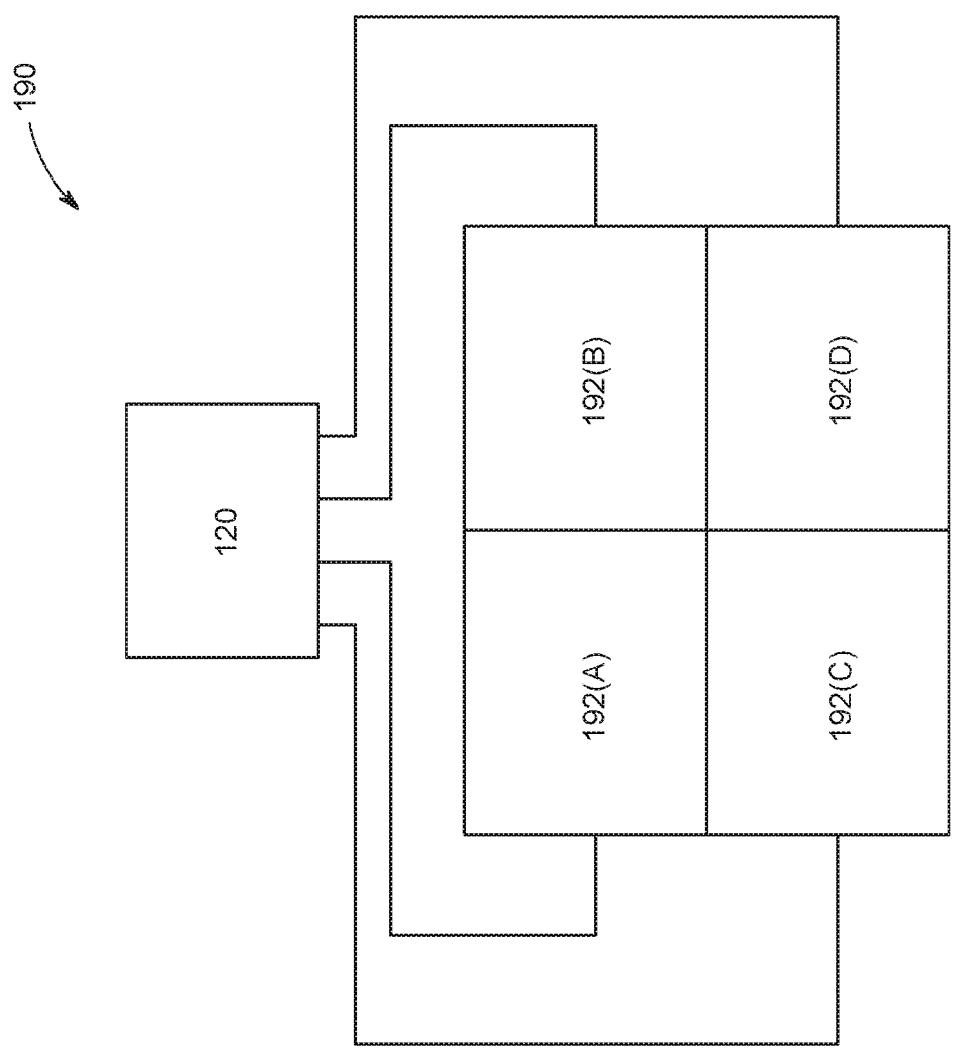
FIG. 10 provides a schematic view of a pixelated detector, according to an embodiment.

FIG. 10 depicts a schematic view of an example pixelated detector 190 formed in accordance with various embodiments. One or more pixelated detectors 190 may be used for example, to provide detectors for a given radiation detector head assembly 115. As seen in FIG. 10, the pixelated detector 190 includes four pixels, 192a, 192b, 192c, 192d. It may be noted that only four pixels are shown in FIG. 10 for ease and clarity of depiction; however, more pixels are utilized in various embodiments. For example, in some embodiments the pixelated detector 190 may include, for example, an array of 64×64 pixels. In some embodiments, each detector includes an array of abutted detector modules, wherein each detector module comprises an array of 16×16 pixels. Further, in some exemplary embodiments of the invention, each detector includes a 2D array of abutted detector modules. For example, a small Field Of View (FOV) detector may have an array of 4×5 modules and a large FOV detector may have an array of 10×14 modules. In some embodiments, each detector comprises a 1D array of abutted detector modules, for example an array of 1×7 modules. As seen in FIG. 10, each of the pixels is independently communicatively coupled to the processing unit 120 (e.g., via a dedicated channel). Accordingly, signals or information received from each pixel may be processed individually by the processing unit 120.

Figure 11:
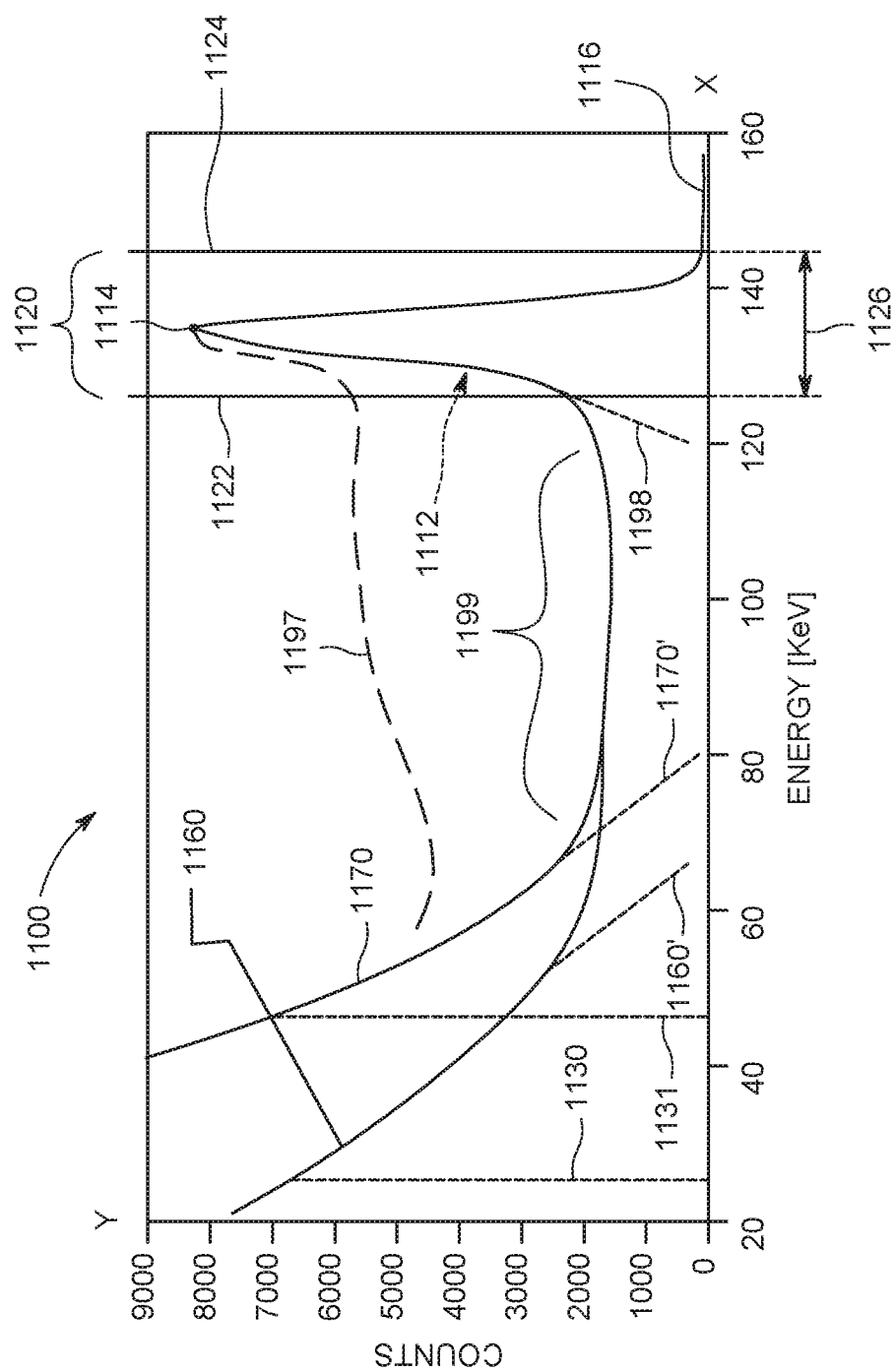
FIG. 11 depicts a spectrum or signal, according to an embodiment.

In various embodiments, signal processing characteristics used to generate event counts from information provided by the pixels may be individually tailored on a per pixel basis. FIG. 11 illustrates an example signal (or spectrum) 1100 using information provided by a pixel. The illustrated example represents use of a Tc99m radioactive source having a single a single energy peak at 140 KeV. The signal 1100 is configured as a plot of count density (counts per KeV). Thus, for a given pixel, all detected events may be provided to the processing unit and be described by the signal 1100. As seen in FIG. 11, the signal 1100 includes a leading edge 1112 that leads to a peak 1114. At energy levels higher than the peak 1114, the number of counts reduces at a trailing portion 1116. An energy "tail" 1199 is caused by a combination of effects, including the following: 1) Compton scattering of radiation within the source, a casing of the source, and structures within the detector (e.g., covers). This effect may be estimated, simulated or measured. 2) Detector incomplete charge collection and other deficiencies. 3) Charge sharing between two adjacent pixels or Compton scattering within the detector crystal. The charge sharing effect, which causes the signal to be divided between two adjacent pixels, may be corrected as detailed for example in United States Patent Application Publication No. 2016/0169737 entitled "SYSTEMS AND METHODS FOR SORTING AND SUMMING SIGNALS FROM AN IMAGING DETECTOR," which is incorporated herein by reference in its entirety. Without the tail 1199, the spectrum would appear as a single, almost symmetric peak continuing along the dashed line 1198. Such a peak shape may be observed in traditional NaI detectors.

Various signal processing characteristics may be used to determine which portion of the signal 1100 (or information provided by a pixel) is used to provide a count that may be used to reconstruct an image (e.g., in conjunction with counts provided by other pixels and/or other detectors). As seen in FIG. 11, a window 1120 includes a lower boundary 1122 and an upper boundary 1124 defining a corresponding width 1126. The peak 1114 is disposed within the window 1120. Generally, counts within the window 1120 may be considered as events that are counted for image reconstruction, with counts outside of the window 1120 discarded. The window 1120 in various embodiments may be asymmetric, with the peak 1114 not located at the center of the window 1120. With a single peak isotope, the location of the upper energy window boundary 1124 may be relatively unimportant, as long as it is located at an energy level high enough to avoid rejection of a significant proportion of events belong to peak 1114; however, when a multi-peak isotope is used, or a multi-isotope image is acquired, the tail of the higher peak may fall within the acceptance window of the lower peak, where it may create false events which may cause image noise, image distortion, and/r artifacts. Accordingly, in such cases, it is desirable to maintain the high energy window boundary 1124 at the lowest energy possible, even if sacrificing a small percentage (for example 1%) of the events in the peak. Generally, in various embodiments, the upper energy window boundary 1124 may be set such that the count density of the peak is comparable to the count density of the tail of all other higher peaks. This position somewhat depends on scattering in the patient, but to a large degree it depends on the shape of the leading edge of the peak. The optimal location of the upper energy window boundary 1124 depends on the characteristics of the pixel, and accordingly it is beneficial to tailor it for each pixel individually.

The optimal location of the lower energy window boundary 1122 may also depend on the characteristics of the pixel (and to some degree on the scatter in the patient), and accordingly it is beneficial to tailor it for each pixel individually as well. Generally, in various embodiments, the lower energy window boundary 1122 may be set such that the count density of the peak is comparable to the count density of the tail. One way to set the lower energy window boundary 1122 is to estimate the energy where the tailing edge 1198 of the peak reaches a predetermined low value (e.g. 10%) compared to its highest level. Alternatively, another example way to set the lower energy window boundary 1122 is to estimate the energy of the lower energy window boundary 1122 that causes the total counts within the energy window to be a preset percentage A (e.g. A=95%) of the counts in an energy window set at 90% of the peak energy. This effectively sets the relative sensitivity of the pixel at 95% of the sensitivity used in the prior art cameras where the lower energy window boundary is set at peak energy −10% and higher energy window boundary is set at peak energy +10% (e.g., 126 to 154 KeV for the Tc99m isotope having a peak at 140 KeV). Such measurements are preferably done with minimal scattering and tail and thus require a radioactive source with minimal scattering. As discussed in connection with FIG. 17, however, such sources are not readily available. Specifically, it is difficult to produce such a source for use with a collimator installed, as a thin flood is required.

Once the lower energy window boundary 1122 and higher energy window boundary 1124 are determined for a specific pixel and a specific isotope, the lower energy window boundary 1122 and higher energy window boundary 1124 may be scaled for other isotopes by a simple shift in energy. For example, for an adjustment to a 140 KeV source, if a specific pixel has a lower energy window boundary 1122 at 116 KeV and higher energy window boundary 1124 at 125.5 KeV (e.g., for cobalt (122 KeV−5%+3%)), boundaries for the given pixel may be set by adding 18 KeV to each boundary to account for the difference of 18 KeV (140−122=18) between the locations of the two peaks. Optionally, each peak may be experimentally calibrated separately. Further optionally, some peaks may be experimentally calibrated separately, and other peaks calibrated by interpolation or extrapolation using the results of peaks experimentally calibrated. It may be noted that, generally, peaks with higher energies tend to have narrower peaks due to smaller relative statistical and electronic noise.

It may be noted that various embodiments disclosed herein use substantially narrower energy windows than prior approaches (at least for the majority of the pixels). As a consequence, the stability of the calibration is relatively more consequential, as a shift of the peak may tend to cause loss of events that may fall outside the narrower energy window. Hence, temperature stabilization is relatively more beneficial than for cameras using relatively wide windows (+/−10%).

It may be noted that, at relatively low energy levels, noise may provide a relatively high number of counts that may overwhelm the processing capability of a system if each of the low energy counts were individually recorded and included, for example, as part of signal 1100. Accordingly, a threshold is set. Events having an energy below the threshold are not recorded or further processed, while events having an energy satisfying the threshold may be recorded and analyzed to determine if they fall within the window 1120 and are to be counted (e.g., for use in image reconstruction). In some embodiments, events within the window 1120 may be counted as events for the particular pixel, while events having an energy lower than the energy level of the lower boundary 1122 of the window 1120 may be considered in conjunction with information from one or more neighboring pixels to determine if there are charge sharing events with one or more neighbors. Various embodiments set the threshold at a lowest possible or practical value for each pixel individually to allow improved counting of low energy split or shared events (events shared between pixels) while avoiding rejection of an undue amount of pixels.

For example, in the illustrated embodiment, two low energy sections of a signal are shown—namely a first low energy section 1160 that corresponds to the low energy portion of a relatively lower noise level pixel, and a second lower energy section 1170 of a more noisy pixel. In the absence of a source, the low energy noise 1160 and 1170 would continue along the dashed lines 1160' and 1170' respectively as seen in FIG. 11. In the illustrated example, desired detector performance and processing capability may be satisfied by keeping a maximum number of counts for the low energy portion of the signal, for example, at 7000 counts (e.g., 7000 counts per a predetermined time period, such as 7000 counts per second). Accordingly, a threshold 1130 for a pixel having the first low energy section 1160 may be set at about 25 KeV. However, the second low energy section 1170 has substantially more than 7000 counts at about 25 KeV. To keep the second low energy section 1170 within a more practical limit, a threshold 1132 for a second pixel corresponding to the second low energy is set at about 50 KeV. Thus, the maximum number of low energy events may be detected for each pixel while keeping the total number of counts within practical levels, and not rejecting an unduly large number of pixels, which would adversely affect manufacturing yield and/or cost. For split event correction (e.g., such as seen in U.S. Patent Application Publication No. 20160169737) to function as effectively as possible, both parts of the split event have to be detected. That is, both parts of the split event in two adjacent pixels must be above the threshold of the pixel in which the part of the split event is detected. Otherwise, at least one of the parts of the split event would not be detected, and the event would not be recovered. For split event correction to work efficiently, the threshold should be set as low as possible in each pixel according to its noise level, without overwhelming the count rate capabilities. It may be noted that with modern computers very high rates may be achieved, for example if parallel processing and data channels are used. The maximum rate per pixel may be estimated by noting the lowest bottleneck in the data rate, and dividing it by the number of pixels. It may be noted that, surprisingly, the number of "false" (random noise) events may be much (even orders of magnitude) higher than the number of events in the peak during clinical imaging without negatively affecting the image quality. This is because such noise events may be at an energy well below the low energy boundary 1122 of the energy window 1120.

It may be noted that the graph seen in FIG. 11 is plotted after energy correction (e.g., after the energy is corrected within the processing unit 1050 according to the energy-correction parameters of each pixel). In some embodiments, to correct the energy, a linear correction may be performed, with the energy of an event related to the signal using the following correction function: Energy=(signal−offset)*gain, wherein the gain and the offset are specific to each pixel (in some embodiments, a quadratic function may be used). However, the thresholding may be done on the uncorrected signal within the module. Accordingly, setting a single uniform value for the threshold for all pixels may cause each pixel to have a different (and somewhat unpredictable) threshold in terms of real (corrected) event energy.

This is yet another example of a benefit of setting the threshold separately for each pixel. In some embodiments, the relation between the threshold setting value and the actual corrected energy threshold may be determined for each pixel. The threshold setting value for a desired corrected energy threshold may then be set for each pixel. Measuring the relation between the threshold setting value and the actual corrected energy threshold may be determined for each pixel by exposing the detector to a source of continuous spectrum, measuring the count density graph, and optionally repeating the measurement at one or more threshold setting values. A source of continuous spectrum may be readily obtained by placing an object with high scattering properties (e.g. a volume of water, or even a few stacks of paper or plastic sheets) between the source and the detector.

Figure 15:
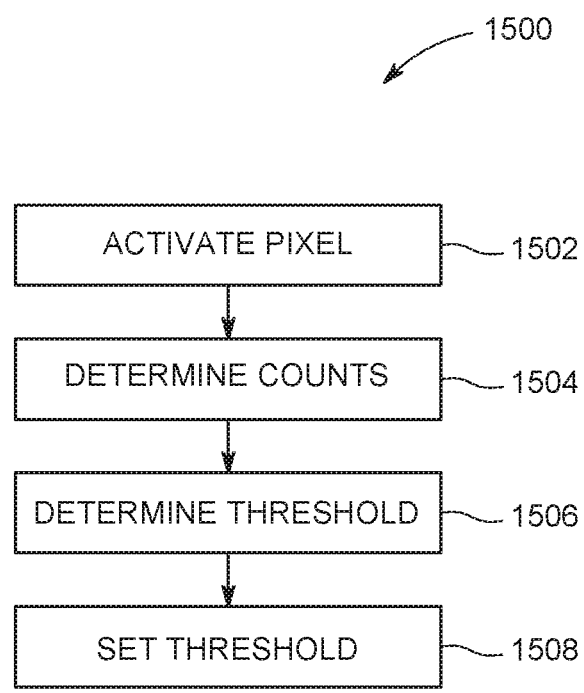
FIG. 15 provides a flowchart of a method, according to an embodiment.

FIG. 15 illustrates a flowchart of a method 1500. The operations of FIG. 15 may be implemented by one or more processors executing program instructions stored in memory. The method 1500, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 1500 may be used as one or more algorithms to direct hardware to perform one or more operations described herein. It should be noted, other methods may be used, in accordance with embodiments herein.

At 1502, a pixel of pixelated detector is activated. The pixel, for example, may not be exposed to a source of radiation, and events from the pixel may be read. With no radiation source, the events read or detected may be understood as noise. In practice, much of the noise encountered resides at lower energy levels (e.g., energy levels substantially lower than peak energy levels encountered during medical imaging).

At 1504, counts are determined. For example, the number of counts detected by the detector may be counted and analyzed on a per time basis (e.g., counts per second). At 1506, a threshold is determined. In the depicted embodiment, the threshold is determined such that a maximum number of counts is not exceeded. At 1508, the threshold for the pixel is set at the level determined at 1506. The process may be repeated for each pixel of the detector, with an individual threshold for each pixel determined and implemented. In some embodiments, the threshold setting process may be repeated for a given pixel on a periodic basis, or may be repeated if a maximum number of counts at low energy for the pixel are determined at a later time (e.g., due to physical changes in the pixel) to exceed the maximum number of counts utilized at 1506.

Returning to FIG. 11, the particular location of the peak 1114 (e.g., highest number of counts) is dependent on the isotope being detected as well as pixel characteristics. For example, for a given isotope, the nominal peak energy value may be 140 kEv. However, some pixels may provide a peak at 120 kEv, some at 140 kEv, some at 160 kEv, and still others at other values. Further, some pixels may provide a relatively narrow band of elevated counts around the peak, while others provide a broader band of elevated counts around the peak.

As discussed herein, signal processing characteristics (e.g., window location and/or width, threshold location) may be individually tailored on a per pixel basis. Because pixels vary from each other, in contrast to conventional approaches that, for example, use the same window and threshold for all pixels, such tailoring provides improved accuracy and reliability, while also increasing pixel yield (e.g., reducing rejection pixels). It may be noted that the pixel characteristics may be individually tailored as part of an initial (and/or periodically performed) calibration process and/or as part of an adjustment made during imaging (e.g., due to variation in pixel performance due to change in temperature).

According to previous approaches, one threshold level is set for all pixels. Such a threshold level is set such that it is well below the low energy boundary 1122 of the energy window 1120 used in the camera. Once the threshold level is set, the count rate in the absence of a radiation source (dark rate) for all energies is measured. An upper level of allowed dark count rate is set at much lower than the rate anticipated during clinical imaging, for example less than a few counts per minute or even less than one count per minute. Each pixel having a dark count rate higher than the allowed dark count rate is marked as "defective" and is turned off. However, the image quality degrades with the number of defective pixels which do not contribute to the image data. If more than a preset number of pixels (e.g. 3) are defective for a given module, the module is marked as defective and is replaced. Such replacement of modules and/or deactivation of pixels adversely affects image quality and/or manufacturing cost (e.g., due to reduced yield caused by rejected modules). Various embodiments disclosed herein, however, change the way defective pixels are defined. According various embodiments, isotope-dependent effective dark count rate is defined as the number of counts per second in the energy window defined in a pixel for the isotope in use. A pixel is deemed defective if the isotope-dependent effective dark count rate is higher than a preset fraction (e.g. 5%) of the rate anticipated within the energy window in a given clinical imaging session. Accordingly, pixels that are considered "defective" for a low energy isotope may be useful for imaging high energy isotopes. Also, pixels that are considered "defective" for a low rate imaging application may be useful for imaging a high rate imaging applications.

For example, the processing unit 120 may be configured to set the threshold for each pixel based on a processing capability. The setting of the threshold may be performed as part of an initial set-up calibration, or as part of a periodically performed calibration to address any changes in detector performance. Each pixel's threshold may be adjusted to provide a total number of recorded or analyzed counts based on the processing capability of the processing unit 120, for example. Pixels that experience more noise at lower energy levels may have their thresholds set relatively high, while pixels that experience less noise at lower energy levels may have their thresholds set relatively lower. Accordingly, noisy pixels may be provided with higher thresholds to reduce noise while still allowing a noisy pixel to be used instead of being rejected or ignored, while less noisy pixels may be provided with a lower threshold, allowing reading of counts at lower energy levels that may be used to count split or shared charges.

The threshold for each pixel may be determined based on the signal produced by the particular pixel along with an overall system processing capability. By way of example, for a system that can process X total counts over a given time period, and that has Y pixels, the number of counts over that time period for a given pixel may be defined as Allowed Counts=X/(Y*Z), where Z is a safety factor. For example, using a safety factor of 2 helps limit the total number of possible counts to half of the system capability. The threshold for each pixel may then be individually set to provide, over the pertinent time period, the Allowed Counts determined above. The setting of the threshold may be performed as part of an initial set-up calibration, or as part of a periodically performed calibration to address any changes in detector performance.

As another example, the processing unit 120 may be configured to set the window for each pixel based on characteristics of the pixel. The location of the upper and lower boundaries and/or the width of the window may be set based on measured or calibrated characteristics of each pixel. For example, a known radiation exposure (e.g., a Cobalt flood) may be exposed to the detector, with each pixel analyzed to measure individual pixel response to the known source.

Past approaches to the setting of windows generally set upper and lower boundaries at energy levels that were a fixed percentage of a peak value or expected peak values (e.g., a lower boundary at an energy level −10% from the peak, and an upper boundary at an energy level +10% of a peak). Various embodiments discussed herein, in contrast, set window boundaries based on characteristics of individual pixels to better track and represent actual signals and/or to provide additional flexibility for movement of a peak (e.g., due to temperature change).

By way of example, the location of the upper boundary of the window may be set to exclude a set percentage of total counts at the highest recorded energies. Then, the lower boundary of the window may be set to provide a comparable sensitivity for energies below the peak. The window width may be set to include a predetermined percentage of total counts obtained over the threshold. For example, in some embodiments, the window width may be set to include 95% of the counts above the threshold. For instance, the upper boundary may be set to exclude the highest 3% of counts above the threshold. Then the lower boundary may be set to exclude the lowest 2% of counts above the threshold. As another example, the lower boundary may be set at distance from the peak corresponding to the distance of the upper boundary of the peak. The distance from the lower boundary to the peak may be the same as the distance from the upper boundary to the peak in examples utilizing a symmetric window, and the distance from the lower boundary to the peak may be different from the distance from the upper boundary to the peak in examples utilizing an asymmetric window. The signal used for calibration may be obtained by deconvolving a known pixel response from a measured signal. As another example, the upper boundary of the window may be set at a given percentage of the peak value (e.g., the upper boundary set where the signal has a higher energy than the peak and is at 3% of the peak number of counts). Similarly, the lower boundary of the window may be set at a given percentage of the peak (e.g., the lower boundary set where the signal has a lower energy than the peak and is at 33% of the peak number of counts). As discussed herein, the window may be set to include a predetermined number of counts relative to a baseline or standard, for example as described in connection with FIG. 16.

Figure 16:
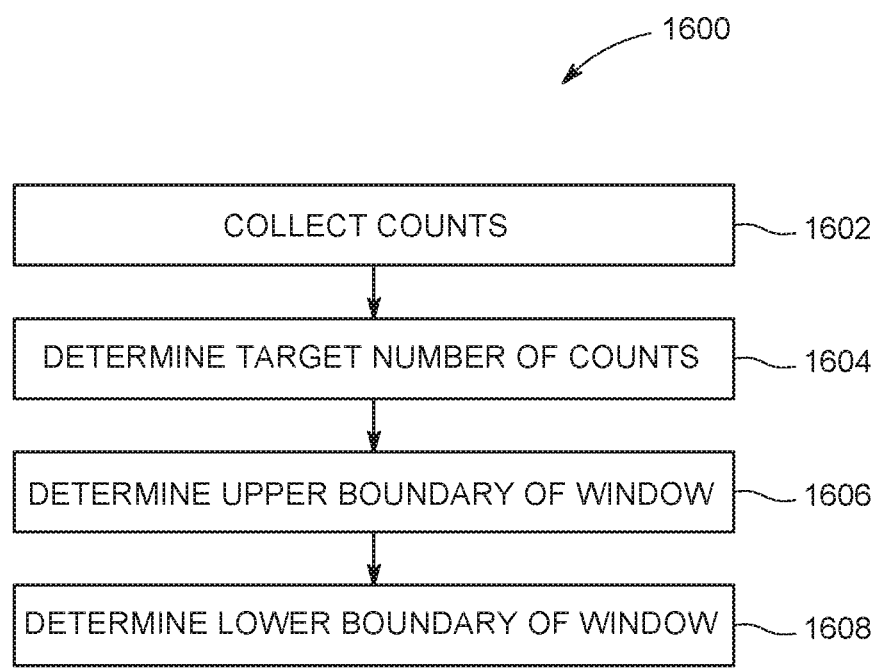
FIG. 16 provides a flowchart of a method, according to an embodiment.

FIG. 16 illustrates a flowchart of a method 1600. The operations of FIG. 16 may be implemented by one or more processors executing program instructions stored in memory. The method 1600, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 1600 may be used as one or more algorithms to direct hardware to perform one or more operations described herein. It should be noted, other methods may be used, in accordance with embodiments herein.

At 1602, counts for a pixel are collected. The counts may be collected as part of an imaging procedure, where an object to be imaged (e.g., a human patient) has been administered an imaging radiopharmaceutical.

At 1604, a target number of counts is determined. For example, the target number of counts may correspond to an area under a signal (e.g., signal 1100) resulting from the collected counts from 1602. For example, a base number of counts (or target area under a signal curve within a window) may be defined by determining the number of counts present when using a predetermined window having a predetermined shape (e.g., a lower boundary at −10% of peak energy and an upper boundary at +10% of peak energy). The target number of counts is then a percentage of the base number counts from the predetermined window (e.g., 90% of counts for predetermined window, 95% of counts for predetermined window, 98% of counts for predetermined window, or 100% of counts for predetermined window, among others). The window may then be set for example, to provide the narrowest window possible that includes the target number of counts.

In the depicted embodiment, at 1606, the upper window is determined. For example, the upper window may be placed at an energy corresponding to a predetermined percentage of peak energy (e.g., 3% or 5%, among others). As another example, the upper window may be placed at an energy level corresponding to a number of counts that correspond to a percentage of peak counts (e.g., 1%, 2%, or 5%, among others).

At 1608, with the target number of counts known and the upper boundary of the window determined, the lower boundary of the window is determined based on the target number of counts. For example, the lower boundary of the window may be determined to provide the target number of counts in cooperation with the upper boundary of the window. In some embodiments, the lower boundary of the window may first be set (e.g., corresponding to a predetermined percentage of peak energy value or peak number of counts), and the upper boundary then determined to provide the target number of counts in cooperation with the lower boundary. The process performed in connection with FIG. 16 may be performed for each pixel, and may be re-performed on a periodic basis or on a continuous basis.

In various embodiments, the processing unit 120 may be configured to adjust a signal processing characteristic (e.g., threshold, window setting) for at least one pixel. The adjustment may be made, for example, during imaging. As another example, the adjustment may be made as part of a periodic or scheduled calibration process. In some embodiments, the adjustment may be made based on a measured external condition (e.g., temperature or change in temperature). In some embodiments, the adjustment may be made based on information provided by a given pixel (e.g., movement of a portion of a signal (e.g., signal 1100) based on information provided by the pixel).

For example, in some embodiments, to address changes in pixel performance, the processing unit 120 may adjust the window 1120 based on a leading edge 1112 of the signal or spectrum 1100 produced by the pixel. For instance, the leading edge 1112 may be defined as a height at a predefined fraction of the height of peak 1114 (e.g., ⅓ of the height of the peak 1114). Then, if the energy level corresponding to the location of the leading edge 1112 changes over time, the position of the window 1120 used to process signal from the pixel may be changed a corresponding amount. For instance, the lower boundary 1122 and upper boundary 1124 may be adjusted by the same amount as the leading edge 1112 has moved from a previous position. Accordingly, if the leading edge 1112 moves to a higher energy (e.g., due to an increase in temperature), the window 1120 may be adjusted to define a higher range of energies. Or, if the leading edge 1112 moves to a lower energy (e.g., due to an increase in temperature), the window 1120 may be adjusted to define a lower range of energies. A leading or rising edge of the signal may beneficially be used in various embodiments as the rising edge may not be affected by scatter. The number of counts used to identify the leading edge may be selected to be higher than a number of counts that may be encountered due to scatter. In other embodiments, other features of the signal 1100 may be used (e.g., peak location) to determine an adjustment. Additionally or alternatively, in addition to window location (e.g., a location of the center of the window) the width 1126 of the window 1120 may be adjusted.

As another example, in some embodiments, to address changes in pixel performance due to a measurable external condition, the window may be adjusted based on a sensed or determined external condition, such as a sensed temperature. For example, each pixel, during a calibration procedure, may be subjected to different temperatures, with the effect of temperature on signal or information output by the pixel analyzed to determine the impact of temperature change on signal characteristics, e.g., peak location and/or corresponding window width. Accordingly, a predetermined relationship between temperature and one or more window features (e.g., location of upper and lower boundaries) may be determined for each pixel. Then, during imaging, information regarding the temperature experienced by each pixel may be provided to the processing unit 120. For example, a temperature sensor associated with each pixel may sense a temperature proximate to a given pixel, provide temperature information to the processing unit 120, and the processing unit 120 may then in response adjust the window used to analyze information from the given pixel an appropriate amount based on the predetermined relationship between temperature and window features. The pixels of the detector(s) of each individual radiation detector head assembly may be adjusted using the temperature sensed by a dedicated temperature sensor disposed on the particular radiation detector head assembly in some embodiments.

Figure 12:
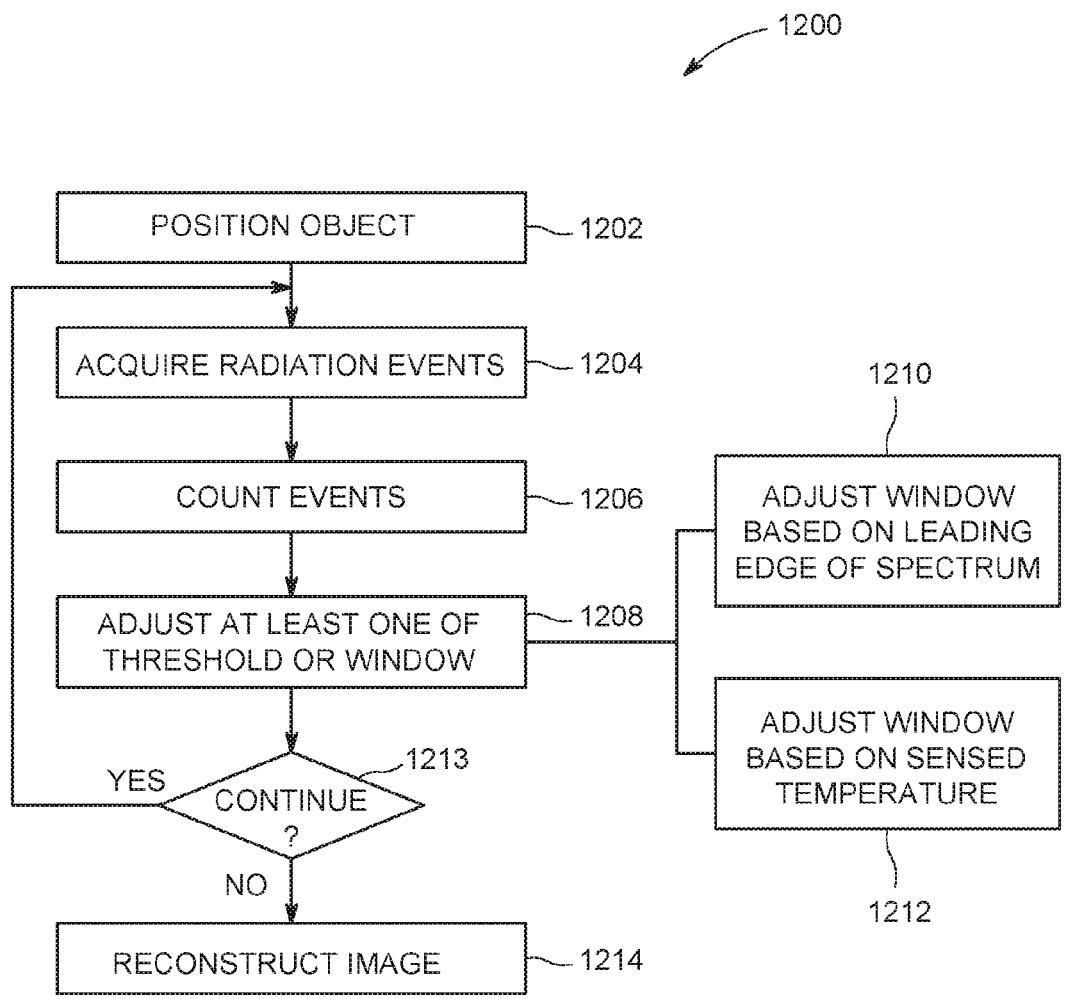
FIG. 12 provides a flowchart of a method, according to an embodiment.

FIG. 12 illustrates a flowchart of a method 1200. The operations of FIG. 12 may be implemented by one or more processors executing program instructions stored in memory. The method 1200, for example, may employ structures or aspects of various embodiments (e.g., systems and/or methods) discussed herein, such as the system 100. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 1200 may be used as one or more algorithms to direct hardware (e.g., processing unit 120) to perform one or more operations described herein. It should be noted, other methods may be used, in accordance with embodiments herein.

At 1202, an object to be imaged is positioned. The object may be a human patient or a portion thereof. The object in various embodiments is disposed in the gantry of an imaging detector having plural detector assemblies (e.g., radiation detector head assemblies 115) having pixelated detectors.

At 1204, radiation events are acquired using the pixelated detectors. In the depicted embodiment, each pixel is individually read. For example, each pixel may have a separate dedicated channel coupling the pixel to one or more processing units. The impact of radiation on the detector results in electrical signals sent to the one or more processors to acquire the radiation events. As the radiation events are acquired, the events may be characterized by their detected energy to provide a signal corresponding to total number of counts plotted against energy level. Events that satisfy a threshold may be retained for further processing and/or consideration, while events that do not satisfy a threshold may not be recorded or retained.

At 1206, with a processing unit (e.g., processing unit 120), events acquired by the pixelated detector are counted. The events are counted on a per pixel basis, with the results used to reconstruct an image. For example, the number of counts over a given time period for a given pixel may be used to determine the appearance of a portion of an image corresponding to the particular pixel. Events that fall within a predefined window (e.g., a range of energies distributed about a peak in the signal) may be counted as true events used for image reconstruction, while events that fall outside of the predefined window are discarded or not counted as true events, and are not used for image reconstruction. (It may be noted that, in embodiments utilizing charge-sharing counting techniques, events that fall outside of the window for neighboring pixels may be combined as appropriate and counted as a joint or shared event between pixels). In the illustrated embodiment, at least one of the threshold or the window are individually tailored for each pixel. For example, to account for variations in low energy noise in pixels (e.g., to prevent processing capabilities from being overwhelmed by large counts of low energy noise while still providing for the ability to count low energy events, for example, as part of a charge-sharing counting technique), each pixel may have an individually set (e.g., as part of a calibration process) threshold. As another example, to account for variance between pixels (e.g., variances in peak location and/or breadth or steepness of spectra or signal of counts vs. energy), the window (e.g., location of upper boundary, location of lower boundary) may be individually set for each window. It may be noted that pixel characteristics (e.g., energy level produced by radiation events) may vary, for example due to changes in Temperature, or due to changes in the detector over time. Accordingly, in various embodiments, signal processing characteristics (e.g., threshold, window) may be changed or adjusted to account for variations. In some embodiments, the changes or adjustments may be made on a per pixel basis.

In the illustrated embodiment, at 1208, at least one of the window or threshold for at least one pixel is adjusted. The adjustment in some embodiments takes place during imaging. Alternatively or additionally, the adjustment may be made while the imaging system is not in use or not scanning a patient. For example, as part of a periodic calibration (e.g., nightly, weekly, monthly), information from one or more scans may be used to track trends in the signal produced by a pixel (e.g., amount of low level noise, position of rising or leading edge of signal) and to make appropriate adjustments. Signal processing characteristics for each pixel may be adjusted individually in various embodiments. As another example, signal processing characteristics may be adjusted based on application type (e.g., high sensitivity vs. high resolution), organ type, and/or patient size, among others.

For example, a first window may be defined for high sensitivity applications where sensitivity is relatively more important, and a second window defined for high resolution where resolution is relatively more important.

It my be noted that using a relatively narrow energy is advantageous for rejecting scattered radiation. However, the narrower the energy window, the lower the sensitivity, since some direct radiation may be rejected as well. Further, dome diagnostic images are more susceptible to scattered radiation than others. For example, when attempting to located "voids" or "cold spots" in an organ, such as non-viable or unhealthy sections in an organ that retains the radiopharmaceuticals, scattered radiation from surrounding tissue may be scattered into the location of the image, masking the lower activity abnormality. In such cases, use of narrow energy windows helps provide better contrast and a superior image. On the other hand, when attempting to locate small peak and a weak "hot spot," such as an active malignant metatastic lesion in a background of low radiation level, use of a somewhat wider window may be useful. Once an energy spectrum of each pixel is measured and retained, new energy windows may be defined without the need to repeat the data acquisition used for generating the energy spectrum. Accordingly, in various embodiments, the energy window (and/or other pixel operation parameters such as the threshold) are selected, varied, and/or adjusted based on the type of the diagnostic imaging procedure.

It may be noted that the threshold and/or window may be adjusted based on observed signal characteristics (e.g., trends or changes in signals produces by a given pixel) and/or based on measured external conditions. For example, in the illustrated embodiment, at 1210, the window is adjusted based on a leading edge of a corresponding spectrum or signal (e.g., signal 1100) produced by a given pixel. The adjustment may be made individually for all pixels of an imaging system or a portion thereof. As another example, in the illustrated embodiment, at 1212, the window is adjusted based on a sensed temperature. For example, each pixel may be calibrated to obtain a predefined relationship defining the pixel's response to temperature change. As the temperature is observed to change (e.g., via a temperature sensor associated with the pixel), the window may be adjusted based on the predefined relationship. Additionally or alternatively, the threshold may be adjusted based on temperature change.

When a patient is imaged, a large portion of the radiation undergoes small angle Compton scattering, and the count density graph may appear generally similarly to dashed line 1197 of FIG. 11. However, a leading edge of peak 1114 may only be slightly affected, and may be used for verification of the position of the peak. Such a determination of peak position requires a large number of counts, and may be done after substantial acquisition time. In various embodiments, events are stored during diagnostic acquisition in a list of events each associated with (at least) its corresponding pixel index and energy. After enough events have been accumulated—during the acquisition, after the acquisition ended, or even after few acquisitions—the position of the leading edge may be determined. If the peak position has shifted enough to cause a degradation of the image, the energy windows may be adjusted and the events in the list re-analyzed according to the new energy windows. Optionally, a calibration source may be used periodically, for example at the end of the day to verify that the calibration is sufficiently accurate. If the calibration is not sufficiently accurate, the energy windows may be adjusted, and the events in the list re-analyzed according to the new energy windows.

It may be noted that even when imaging a patient injected with a multi-peak isotope, or multiple isotopes, the leading edge of the peak with the highest energy may be easily analyzed as it is unaffected by the other peaks. Optionally, position of the leading edges of lower energy peaks may also be accurately determined.

At 1213, it is determined if the scan is to continue, or if more events are to be acquired. If so, the method 1200 may return to 1204 to acquire additional events using the adjustments of 1208. If no more imaging information is to be acquired, the method 1200 proceeds to 1214.

At 1214, an image is reconstructed. For example, one or more processors (e.g., processing unit 120) may utilize the counts determined per pixel to reconstruct an image. For example, the appearance (e.g., the shade or color) of a portion of an image corresponding to a given pixel may be determined using the true events counted for that particular pixel.

Figure 17:
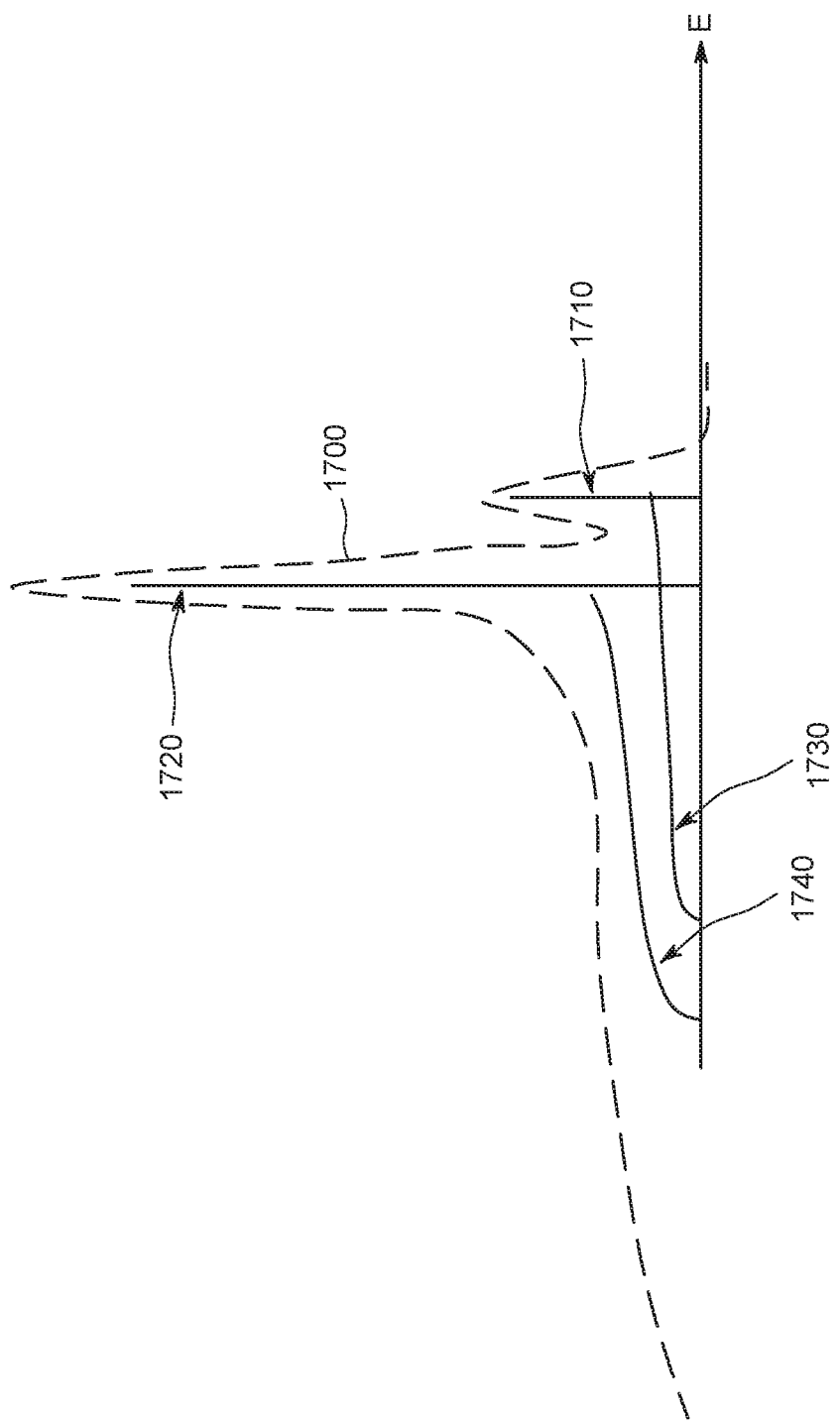
FIG. 17 depicts a signal for deconvolution, according to an embodiment.

It may be noted that, as part of a calibration or re-calibration procedure, knowledge of the true energy response of a pixel may be utilized for qualifying the pixel and for correctly setting an energy window for the pixel during imaging. To measure a true energy response, a pure single-peak source may be employed; however, such sources may be difficult to obtain and/or use in the field. Cobalt, which may for example be utilized in the field, has two peaks. In various embodiments, the energy response of the pixel may be obtained by computing a deconvolution process with a known true spectrum of the source. With reference to FIG. 17, a measured signal 1700 (e.g., from a 2 peak calibration source such as Cobalt) may be deconvolved to recover a single energy source curve for calibration, using the assumption that the energy response function remains essentially similar for different peak energies, with the response shifting with different peak energy levels. In FIG. 17, the measured signal 1700 may be understood as the result of the convolution of a known emission of Cobalt with the energy response of the pixel. In FIG. 17, contributions to the measured signal 1700 include the first cobalt peak 1710, the second peak 1720, first scatter 1730 of the first peak 1710, and second scatter 1740 of the second peak 1720. By deconvolving the measured signal 1700 with the known emission of the radiation source (e.g., first cobalt peak 1710, second peak 1720, first scatter 1730 of first peak 1710, and second scatter 1740 of second scatter 1720), the energy response of the pixel may be determined and used for calibration. One or more aspects of the calibration may be performed according to the process discussed above in connection with FIG. 11, wherein the result of the deconvolution is used instead of the measured spectrum. Generally, the contribution of the first peak 1710 and the second peak 1720 are well known, and the contribution of the first scatter 1730 of the first peak 1710 and the second scatter 1740 of the second peak 1720 may be measured once with a high resolution detector (e.g. cooled Ge detector), or estimated for a specific type of calibration source.

In Gamma cameras, the acquired image may undergo a sensitivity correction calibration to account for variability in the size and sensitivity of each pixel and variability of the collimator bores. According to various embodiments, sensitivity may be calibrated for the actual energy windows used. Thus, if a cobalt source is used, the deconvolution process used for calibration may be performed before the sensitivity calibration. Similarly, if, for a specific type of imaging, the threshold is readjusted, or a specific pixel is turned off the sensitivity of said specific pixel and its neighbors may be adjusted since the efficiency of the split correction algorithm will be affected. Accordingly, in various embodiments, a sensitivity calibration may be adjusted based on the energy window used, without the need to repeat the data acquisition used for generating the energy spectrum.

It may be noted that, in some embodiments, a periodic calibration or adjustment may be performed using list mode data from one or more scans at a post-processing stage, to confirm and/or update window settings. An example of a method including post-acquisition adjustment of window setting is provided by FIG. 18.

Figure 18:
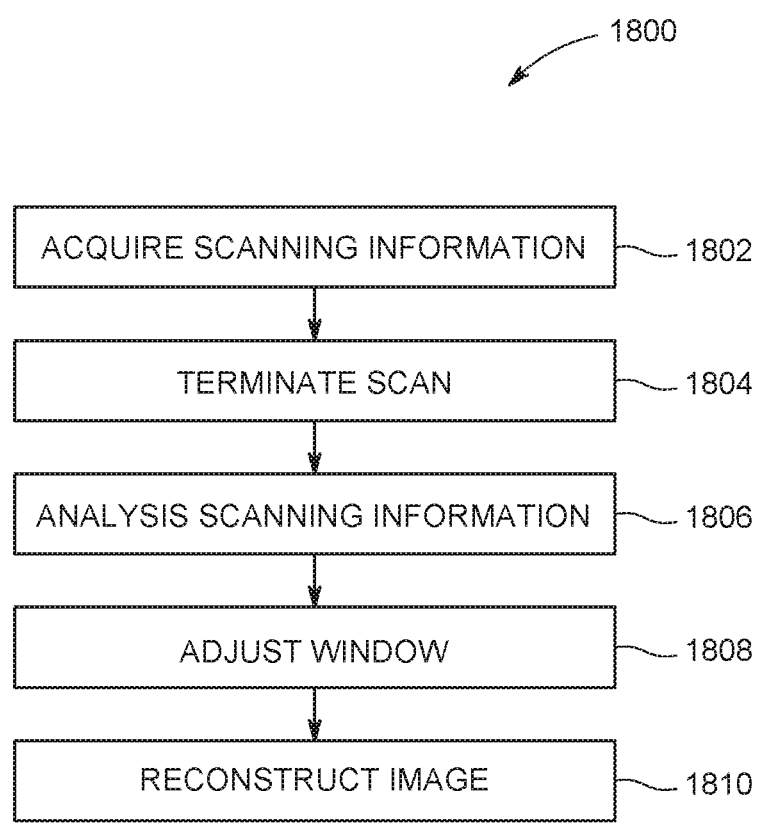
FIG. 18 provides a flowchart of a method, according to an embodiment.

FIG. 18 illustrates a flowchart of a method 1800. The operations of FIG. 18 may be implemented by one or more processors executing program instructions stored in memory. The method 1800, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 1800 may be used as one or more algorithms to direct hardware to perform one or more operations described herein. It should be noted, other methods may be used, in accordance with embodiments herein.

At 1802, scanning information is acquired. The information may be acquired, for example, with a scanning system including multiple detector heads configured to detect radiation from an object (e.g., a human patient that has been administered a radioactive imaging pharmaceutical).

At 1804, the scan is terminated. For example, after a desired time period, or after a desired number of counts have been acquired, the detector heads may be de-activated and the object removed from the scanning system.

At 1806, at some point after the scan has been terminated, the scanning information is analyzed. The scanning information may be analyzed, for example, in a list mode. Generally, the scanning information is analyzed to identify and adjust for any movement in observed energy levels corresponding to one or more peaks of a radioactive isotope.

At 1808, a window (e.g., window 1120) for analyzing imaging data is adjusted. For example, the window may be adjusted based on a shift or change in the rising edge or leading edge of a signal leading up to a peak. By adjusting the window at 1808, various embodiments provide a fail-safe post acquisition checking of energy window position, or a back-up to ensure accurate peak tracking. The window may be adjusted on a per-pixel basis. If, for the given pixel, the peak remains within the window or a desired portion of the window, no adjustment need be made. However, for any pixels where the peak does not remain within the window or desired portion of the window, the window may be adjusted to include the peak as desired. Accordingly, changes in peak that are not detected by a sensor or otherwise not addressed in real-time or near real-time, may still be accounted for in various embodiments. It may be noted that, for a given pixel, multiple adjustments of the window may be made corresponding to changes of the peak during the acquisition.

At 1810, an image is reconstructed. In the depicted embodiment, the image is reconstructed using the scanning information acquired at 1802 and the window adjustment(s) determined at 1808.

The embodiments described above and illustrated by FIGS. 1-12 may be implemented in medical imaging systems, such as, for example, SPECT, SPECT-CT, PET and PET-CT. Various methods and/or systems (and/or aspects thereof) described herein may be implemented using a medical imaging system. For example, FIG. 13 is a schematic illustration of a NM imaging system 1000 having a plurality of imaging detector head assemblies mounted on a gantry (which may be mounted, for example, in rows, in an iris shape, or other configurations, such as a configuration in which the movable detector carriers 1016 are aligned radially toward the patient-body 1010). It should be noted that the arrangement of FIG. 13 is provided by way of example for illustrative purposes, and that other arrangements (e.g., detector arrangements) may be employed in various embodiments. In the illustrated example, a plurality of imaging detectors 1002 are mounted to a gantry 1004. In the illustrated embodiment, the imaging detectors 1002 are configured as two separate detector arrays 1006 and 1008 coupled to the gantry 1004 above and below a subject 1010 (e.g., a patient), as viewed in FIG. 13. The detector arrays 1006 and 1008 may be coupled directly to the gantry 1004, or may be coupled via support members 1012 to the gantry 1004 to allow movement of the entire arrays 1006 and/or 1008 relative to the gantry 1004 (e.g., transverse translating movement in the left or right direction as viewed by arrow T in FIG. 13). Additionally, each of the imaging detectors 1002 includes a detector unit 1014, at least some of which are mounted to a movable detector carrier 1016 (e.g., a support arm or actuator that may be driven by a motor to cause movement thereof) that extends from the gantry 1004. In some embodiments, the detector carriers 1016 allow movement of the detector units 1014 towards and away from the subject 1010, such as linearly. Thus, in the illustrated embodiment the detector arrays 1006 and 1008 are mounted in parallel above and below the subject 1010 and allow linear movement of the detector units 1014 in one direction (indicated by the arrow L), illustrated as perpendicular to the support member 1012 (that are coupled generally horizontally on the gantry 1004). However, other configurations and orientations are possible as described herein. It should be noted that the movable detector carrier 1016 may be any type of support that allows movement of the detector units 1014 relative to the support member 1012 and/or gantry 1004, which in various embodiments allows the detector units 1014 to move linearly towards and away from the support member 1012.

Each of the imaging detectors 1002 in various embodiments is smaller than a conventional whole body or general purpose imaging detector. A conventional imaging detector may be large enough to image most or all of a width of a patient's body at one time and may have a diameter or a larger dimension of approximately 50 cm or more. In contrast, each of the imaging detectors 1002 may include one or more detector units 1014 coupled to a respective detector carrier 1016 and having dimensions of for example, 4 cm to 20 cm and may be formed of Cadmium Zinc Telluride (CZT) tiles or modules. For example, each of the detector units 1014 may be 8×8 cm in size and be composed of a plurality of CZT pixelated modules (not shown). For example, each module may be 4×4 cm in size and have 16×16=256 pixels (pixelated anodes). In some embodiments, each detector unit 1014 includes a plurality of modules, such as an array of 1×7 modules. However, different configurations and array sizes are contemplated including, for example, detector units 1014 having multiple rows of modules.

It should be understood that the imaging detectors 1002 may be different sizes and/or shapes with respect to each other, such as square, rectangular, circular or other shape. An actual field of view (FOV) of each of the imaging detectors 1002 may be directly proportional to the size and shape of the respective imaging detector.

The gantry 1004 may be formed with an aperture 1018 (e.g., opening or bore) therethrough as illustrated. A patient table 1020, such as a patient bed, is configured with a support mechanism (not shown) to support and carry the subject 1010 in one or more of a plurality of viewing positions within the aperture 1018 and relative to the imaging detectors 1002. Alternatively, the gantry 1004 may comprise a plurality of gantry segments (not shown), each of which may independently move a support member 1012 or one or more of the imaging detectors 1002.

The gantry 1004 may also be configured in other shapes, such as a "C", "H" and "L", for example, and may be rotatable about the subject 1010. For example, the gantry 1004 may be formed as a closed ring or circle, or as an open arc or arch which allows the subject 1010 to be easily accessed while imaging and facilitates loading and unloading of the subject 1010, as well as reducing claustrophobia in some subjects 1010.

Additional imaging detectors (not shown) may be positioned to form rows of detector arrays or an arc or ring around the subject 1010. By positioning multiple imaging detectors 1002 at multiple positions with respect to the subject 1010, such as along an imaging axis (e.g., head to toe direction of the subject 1010) image data specific for a larger FOV may be acquired more quickly.

Each of the imaging detectors 1002 has a radiation detection face, which is directed towards the subject 1010 or a region of interest within the subject.

The collimators 1022 (and detectors) in FIG. 13 are depicted for ease of illustration as single collimators in each detector head. Optionally, for embodiments employing one or more parallel-hole collimators, multi-bore collimators may be constructed to be registered with pixels of the detector units 1014, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in-between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 1030 may control the movement and positioning of the patient table 1020, imaging detectors 1002 (which may be configured as one or more arms), gantry 1004 and/or the collimators 1022 (that move with the imaging detectors 1002 in various embodiments, being coupled thereto). A range of motion before or during an acquisition, or between different image acquisitions, is set to maintain the actual FOV of each of the imaging detectors 1002 directed, for example, towards or "aimed at" a particular area or region of the subject 1010 or along the entire subject 1010. The motion may be a combined or complex motion in multiple directions simultaneously, concurrently, or sequentially.

The controller unit 1030 may have a gantry motor controller 1032, table controller 1034, detector controller 1036, pivot controller 1038, and collimator controller 1040. The controllers 1030, 1032, 1034, 1036, 1038, 1040 may be automatically commanded by a processing unit 1050, manually controlled by an operator, or a combination thereof. The gantry motor controller 1032 may move the imaging detectors 1002 with respect to the subject 1010, for example, individually, in segments or subsets, or simultaneously in a fixed relationship to one another. For example, in some embodiments, the gantry controller 1032 may cause the imaging detectors 1002 and/or support members 1012 to move relative to or rotate about the subject 1010, which may include motion of less than or up to 180 degrees (or more).

The table controller 1034 may move the patient table 1020 to position the subject 1010 relative to the imaging detectors 1002. The patient table 1020 may be moved in up-down directions, in-out directions, and right-left directions, for example. The detector controller 1036 may control movement of each of the imaging detectors 1002 to move together as a group or individually. The detector controller 1036 also may control movement of the imaging detectors 1002 in some embodiments to move closer to and farther from a surface of the subject 1010, such as by controlling translating movement of the detector carriers 1016 linearly towards or away from the subject 1010 (e.g., sliding or telescoping movement). Optionally, the detector controller 1036 may control movement of the detector carriers 1016 to allow movement of the detector array 1006 or 1008. For example, the detector controller 1036 may control lateral movement of the detector carriers 1016 illustrated by the T arrow (and shown as left and right as viewed in FIG. 10). In various embodiments, the detector controller 1036 may control the detector carriers 1016 or the support members 1012 to move in different lateral directions. Detector controller 1036 may control the swiveling motion of detectors 1002 together with their collimators 1022. In some embodiments, detectors 1002 and collimators 1022 may swivel or rotate around an axis.

The pivot controller 1038 may control pivoting or rotating movement of the detector units 1014 at ends of the detector carriers 1016 and/or pivoting or rotating movement of the detector carrier 1016. For example, one or more of the detector units 1014 or detector carriers 1016 may be rotated about at least one axis to view the subject 1010 from a plurality of angular orientations to acquire, for example, 3D image data in a 3D SPECT or 3D imaging mode of operation. The collimator controller 1040 may adjust a position of an adjustable collimator, such as a collimator with adjustable strips (or vanes) or adjustable pinhole(s).

It should be noted that motion of one or more imaging detectors 1002 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 1036 and pivot controller 1038 may be combined to provide the different movements described herein.

Prior to acquiring an image of the subject 1010 or a portion of the subject 1010, the imaging detectors 1002, gantry 1004, patient table 1020 and/or collimators 1022 may be adjusted, such as to first or initial imaging positions, as well as subsequent imaging positions. The imaging detectors 1002 may each be positioned to image a portion of the subject 1010. Alternatively, for example in a case of a small size subject 1010, one or more of the imaging detectors 1002 may not be used to acquire data, such as the imaging detectors 1002 at ends of the detector arrays 1006 and 1008, which as illustrated in FIG. 13 are in a retracted position away from the subject 1010. Positioning may be accomplished manually by the operator and/or automatically, which may include using, for example, image information such as other images acquired before the current acquisition, such as by another imaging modality such as X-ray Computed Tomography (CT), MRI, X-Ray, PET or ultrasound. In some embodiments, the additional information for positioning, such as the other images, may be acquired by the same system, such as in a hybrid system (e.g., a SPECT/CT system). Additionally, the detector units 1014 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 1002, gantry 1004, patient table 1020, and/or collimators 1022 are positioned, one or more images, such as three-dimensional (3D) SPECT images are acquired using one or more of the imaging detectors 1002, which may include using a combined motion that reduces or minimizes spacing between detector units 1014. The image data acquired by each imaging detector 1002 may be combined and reconstructed into a composite image or 3D images in various embodiments.

In one embodiment, at least one of detector arrays 1006 and/or 1008, gantry 1004, patient table 1020, and/or collimators 1022 are moved after being initially positioned, which includes individual movement of one or more of the detector units 1014 (e.g., combined lateral and pivoting movement) together with the swiveling motion of detectors 1002. For example, at least one of detector arrays 1006 and/or 1008 may be moved laterally while pivoted. Thus, in various embodiments, a plurality of small sized detectors, such as the detector units 1014 may be used for 3D imaging, such as when moving or sweeping the detector units 1014 in combination with other movements.

In various embodiments, a data acquisition system (DAS) 1060 receives electrical signal data produced by the imaging detectors 1002 and converts this data into digital signals for subsequent processing. However, in various embodiments, digital signals are generated by the imaging detectors 1002. An image reconstruction device 1062 (which may be a processing device or computer) and a data storage device 1064 may be provided in addition to the processing unit 1050. It should be noted that one or more functions related to one or more of data acquisition, motion control, data processing and image reconstruction may be accomplished through hardware, software and/or by shared processing resources, which may be located within or near the imaging system 1000, or may be located remotely. Additionally, a user input device 1066 may be provided to receive user inputs (e.g., control commands), as well as a display 1068 for displaying images. DAS 1060 receives the acquired images from detectors 1002 together with the corresponding lateral, vertical, rotational and swiveling coordinates of gantry 1004, support members 1012, detector units 1014, detector carriers 1016, and detectors 1002 for accurate reconstruction of an image including 3D images and their slices.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the term "computer," "processor," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer," "processor," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. An imaging system comprising:
   a gantry having a bore therethrough;
   plural radiation detector head assemblies disposed about the bore of the gantry, each radiation detector head assembly comprising
      a detector housing; and
      a rotor assembly disposed within the detector housing and configured to be rotated about an axis, the rotor assembly comprising a detector unit comprising an absorption member and associated processing circuitry, wherein the absorption member and the associated processing circuitry are disposed within the detector housing;
   a cooling unit mounted to the gantry and configured to provide an output flow of air at a controlled temperature; and
   a manifold coupled to the cooling unit and the plural radiation detector head assemblies placing the cooling unit and plural radiation detector head assemblies in fluid communication with each other, wherein the output flow of air from the cooling unit is delivered via the manifold to the detector housings of the plural radiation detector head assemblies.

2. The imaging system of claim 1, wherein the cooling unit comprises a thermoelectric chiller (TEC).

3. The imaging system of claim 1, wherein the cooling unit receives an inlet flow from an atmospheric source.

4. The imaging system of claim 1, wherein the cooling unit receives an exhaust flow from the plural radiation detector head assemblies.

5. The imaging system of claim 1, wherein the rotor assembly comprises a casing and fins extending along an exterior surface of the casing, wherein the fins are configured to have variable heat transfer capability along a length of the rotor assembly.

6. The imaging system of claim 5, wherein the fins have a variable height along the length of the rotor assembly.

7. The imaging system of claim 5, wherein at least some of the fins have different fin lengths, wherein the number of fins varies along the length of the rotor assembly.

8. The imaging system of claim 5, wherein the fins have a variable thermal conductivity along the length of the rotor assembly.

9. The imaging system of claim 1, wherein the absorption member includes a pixelated detector having individually read pixels, wherein the imaging system further comprises a processing unit comprising one or more processors and at least one memory comprising a tangible and non-transitory computer readable storage medium including instructions configured to instruct the one or more processors to count events detected by the detector units using a corresponding threshold and window for each pixel, wherein at least one of the threshold or the window are individually tailored for each pixel.

10. The imaging system of claim 9, wherein the instructions are further configured to instruct the one or more processors to adjust at least one of the threshold or the window for at least one pixel during imaging.

11. An imaging system comprising:
a pixelated detector having individually read pixels; and
a processing unit comprising one or more processors and at least one memory comprising a tangible and non-transitory computer readable storage medium including instructions configured to instruct the one or more processors to count events detected by the detector units using a corresponding threshold and window for each pixel, wherein at least one of the threshold or the window are individually tailored for each pixel, wherein the window is an energy window defined by an upper energy boundary corresponding to a higher energy level and a lower energy boundary corresponding to a lower energy level, wherein at least one of the upper energy boundary or the lower energy boundary of the window is adjusted based on a leading edge of a corresponding spectrum produced by the at least one pixel, the leading edge defined at a predefined fraction of a height of a peak of the spectrum.

12. The imaging system of claim 11, wherein the instructions are further configured to instruct the one or more processors to adjust at least one of the threshold or the window for at least one pixel during imaging.

13. The imaging system of claim 12, wherein the instructions are further configured to instruct the one or more processors to adjust the window based on a sensed temperature.

14. The imaging system of claim 11, wherein the instructions are further configured to instruct the one or more processors to individually set the threshold for each pixel based on a processing capability.

15. The imaging system of claim 11, wherein the instructions are further configured to instruct the one or more processors to individually set the window for each pixel based on characteristics of the pixel.

16. A method comprising:
acquiring radiation events with a pixelated detector having individually read pixels; and
counting, with a processing unit comprising at least one processor, the events detected by the pixelated detector using a corresponding threshold and window for each pixel, wherein at least one of the threshold or the window are individually tailored for each pixel, wherein the window is an energy window defined by an upper energy boundary corresponding to a higher energy level and a lower energy boundary corresponding to a lower energy level, wherein at least one of the upper energy boundary or the lower energy boundary of the window is adjusted based on a leading edge of a corresponding spectrum produced by the at least one pixel, the leading edge defined at a predefined fraction of a height of a peak of the spectrum.

17. The method of claim 16, further comprising adjusting at least one of the threshold or the window for at least one pixel during imaging.

18. The method of claim 17, further comprising adjusting the window based on a leading edge of a corresponding spectrum produced by the at least one pixel.

19. The method of claim 17, further comprising adjusting the window based on a sensed temperature.

* * * * *